(12) United States Patent
Zhang et al.

(10) Patent No.: US 9,598,384 B2
(45) Date of Patent: Mar. 21, 2017

(54) 3-(2-AMINO-ETHYL)-ALKYLIDENE)-THIAZOLIDINE-2,4-DIONE AND 1-(2-AMINO-ETHYL)-ALKYLIDENE-1,3-DIHYDRO-INDOL-2-ONE DERIVATIVES AS SELECTIVE SPHINGOSINE KINASE 2 INHIBITORS

(71) Applicant: VIRGINIA COMMONWEALTH UNIVERSITY, Richmond, VA (US)

(72) Inventors: Shijun Zhang, Richmond, VA (US); Sarah Spiegel, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 14/933,042

(22) Filed: Nov. 5, 2015

(65) Prior Publication Data
US 2016/0159758 A1    Jun. 9, 2016

Related U.S. Application Data

(62) Division of application No. 14/377,205, filed as application No. PCT/US2013/025093 on Feb. 7, 2013, now abandoned.

(60) Provisional application No. 61/597,344, filed on Feb. 10, 2012.

(51) Int. Cl.
  *C07D 209/34* (2006.01)
  *C07D 209/44* (2006.01)
  *C07D 277/34* (2006.01)

(52) U.S. Cl.
  CPC ......... *C07D 277/34* (2013.01); *C07D 209/34* (2013.01)

(58) Field of Classification Search
  CPC .................................................. C07D 209/34
  USPC .......................................................... 548/486
  See application file for complete search history.

(56) References Cited

U.S. PATENT DOCUMENTS

| | | | |
|---|---|---|---|
| 8,877,946 B2 * | 11/2014 | Go ........................ | A61K 31/404 548/483 |
| 2011/0071195 A1 * | 3/2011 | Chen .................... | C07D 209/34 514/339 |
| 2011/0135594 A1 * | 6/2011 | Graupe ................ | C07D 209/34 424/85.1 |
| 2011/0166191 A1 | 7/2011 | Zhang | |
| 2011/0263565 A1 * | 10/2011 | Treu ..................... | C07D 209/34 514/210.21 |

FOREIGN PATENT DOCUMENTS

CN    102070555 A    5/2011

OTHER PUBLICATIONS

Liu et al. 3,5-Disubstituted-thiazoldine-2,4-dione analogs as anti-cancer agents: Design, synthesis and biological characterization. European Journal of Medicinal Chemistry (2012), 47, 125-137.

\* cited by examiner

*Primary Examiner* — Nyeemah A Grazier
(74) *Attorney, Agent, or Firm* — Whitham, Curtis & Cook, P.C.

(57) ABSTRACT

3-(2-amino-ethyl)-5-[3-(4-substituted-phenyl)-alkylidene)-thiazolidine-2,4-dione and 1-(2-amino-ethyl)-3-alkylidene-1,3-dihydro-indol-2-one and derivatives thereof are provided for use as selective SphK2 inhibitors and for use in the treatment of human diseases, such as cancer.

12 Claims, 14 Drawing Sheets

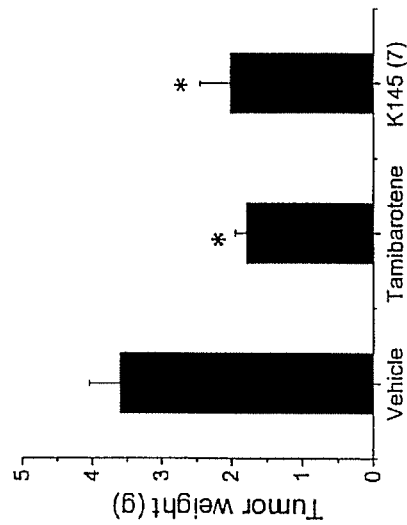
Figure 13A
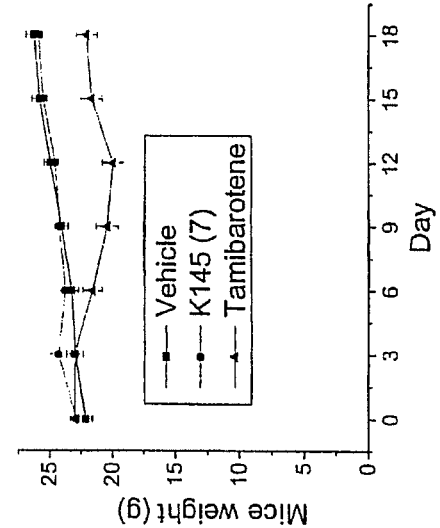
Figure 13B
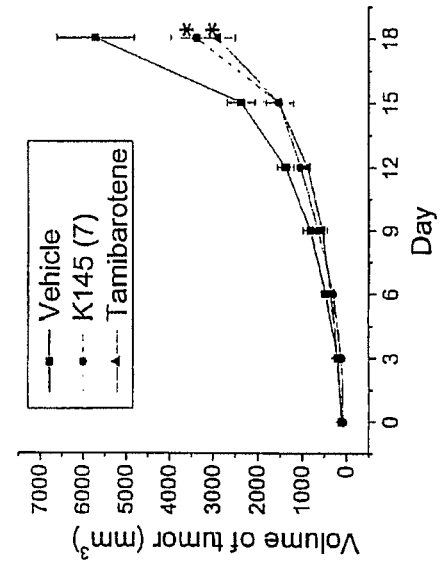
Figure 13C
Figure 13D

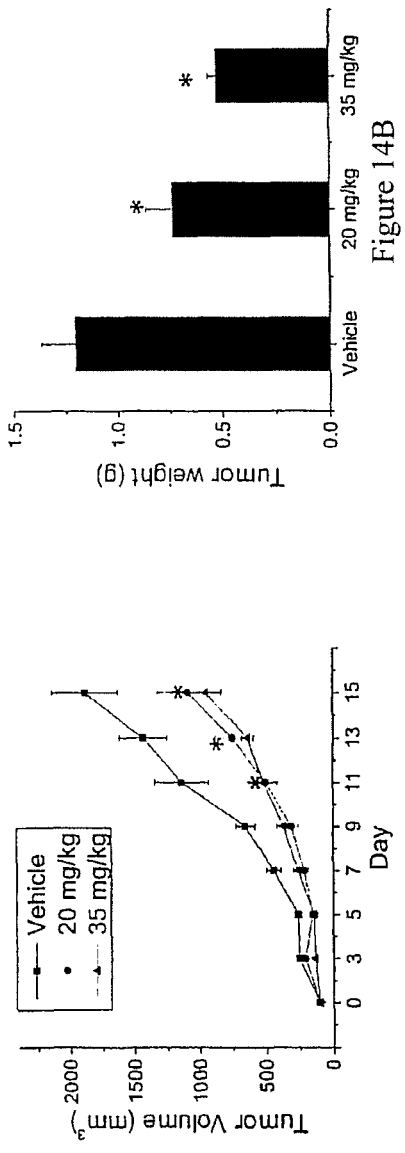
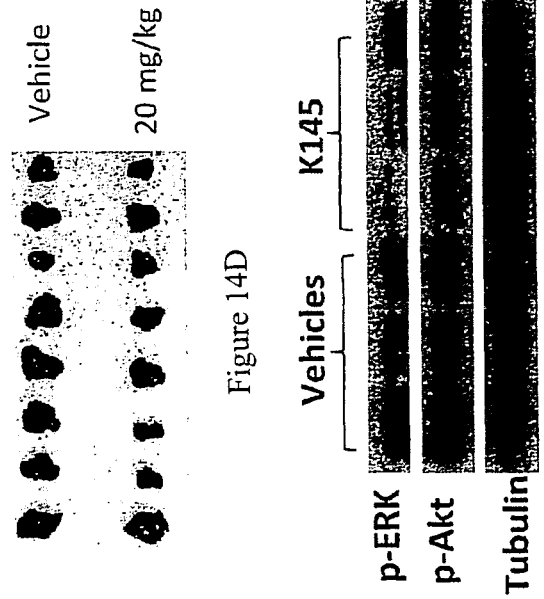
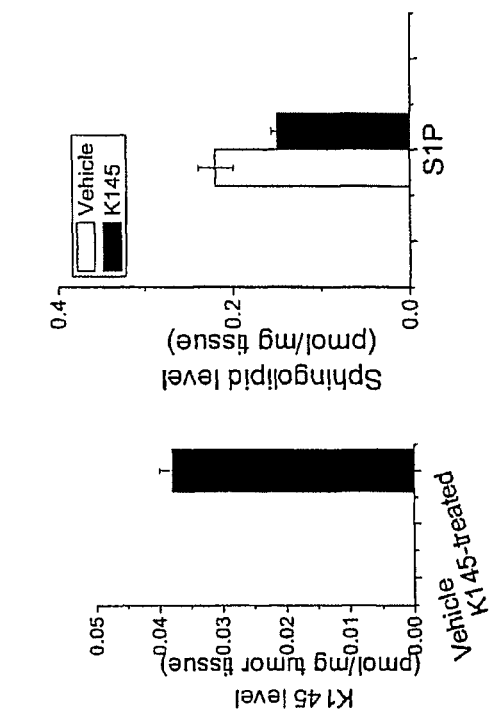
Figure 14A
Figure 14B
Figure 14C
Figure 14D
Figure 14E

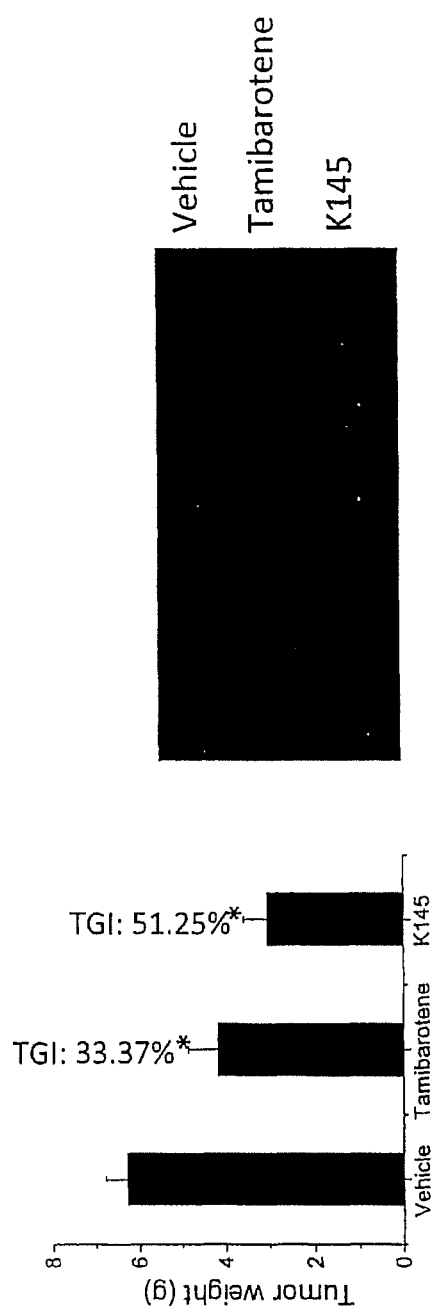
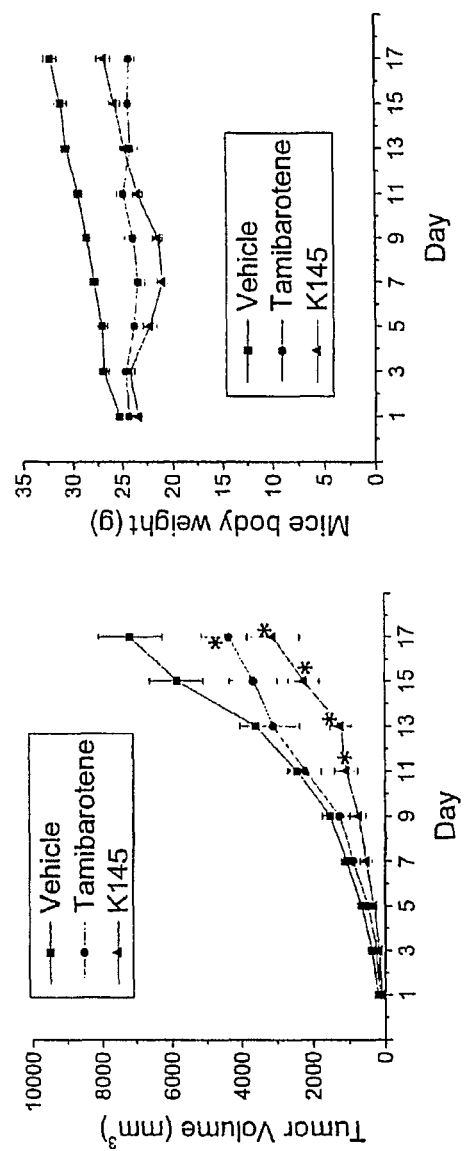
Figure 15A
Figure 15B
Figure 15C
Figure 15D

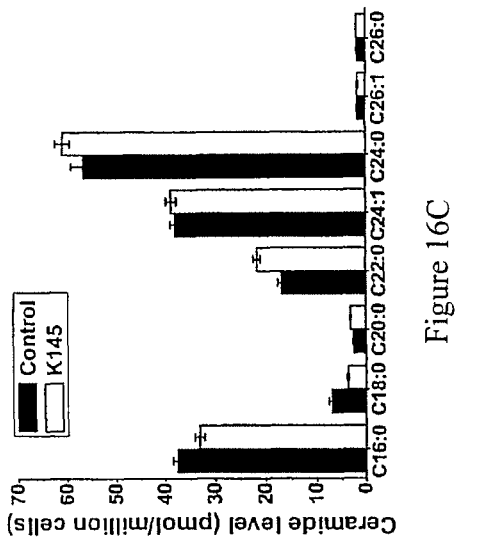
Figure 16A
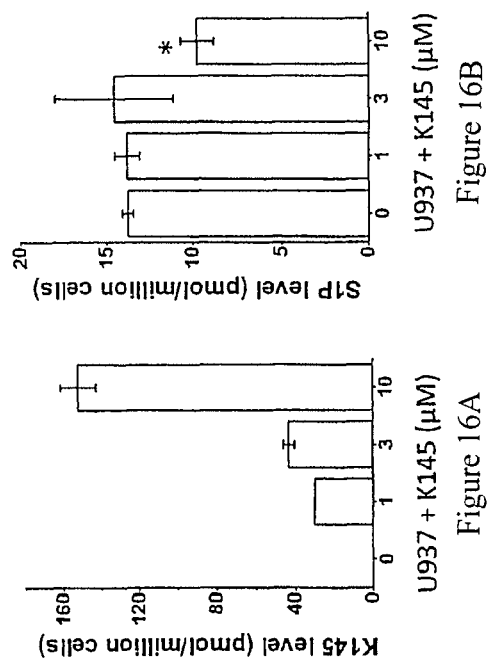
Figure 16D
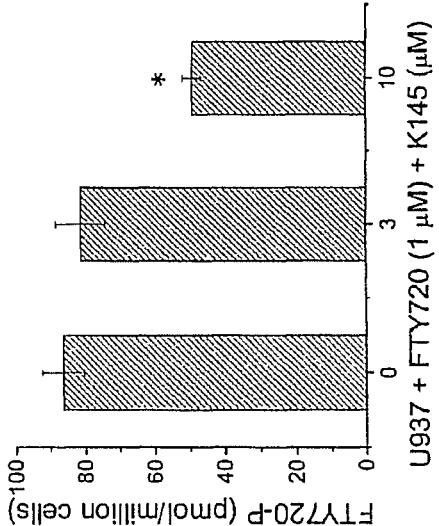
Figure 16B
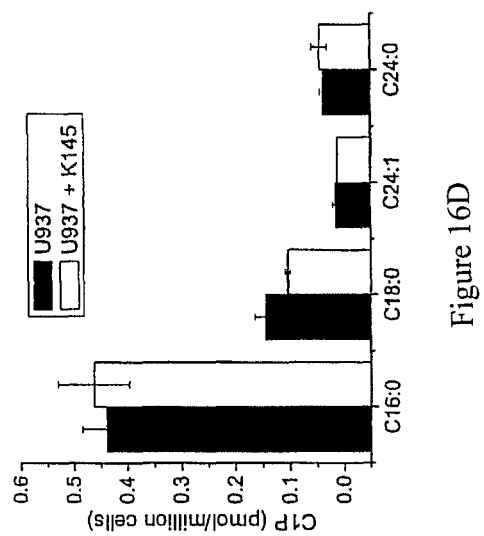
Figure 16C
Figure 16E

3-(2-AMINO-ETHYL)-ALKYLIDENE)-THIAZOLIDINE-2,4-DIONE AND 1-(2-AMINO-ETHYL)-ALKYLIDENE-1,3-DIHYDRO-INDOL-2-ONE DERIVATIVES AS SELECTIVE SPHINGOSINE KINASE 2 INHIBITORS

CROSS-REFERENCE TO RELATED APPLICATIONS

This application is a divisional of U.S. Ser. No. 14/377,205 filed Aug. 7, 2014, which itself was a Rule 371 filing from PCT/US2013/025093 filed Feb. 7, 2013, and claims priority to U.S. Ser. No. 61/597,344 filed Feb. 10, 2012.

BACKGROUND OF THE INVENTION

Field of the Invention

The invention generally relates to 5-alkylidenethiazolidine-2,4-dione and 3-alkylidene-1,3-dihydro-indol-2-one analogs and their use as selective sphingosine kinase 2 (SphK2) inhibitors in clinical implications. In particular, the invention provides 5-alkylidenethiazolidine-2,4-dione and 3-alkylidene-1,3-dihydro-indol-2-one analogs and derivatives thereof as SphK2 inhibitors and for use in the treatment of cancer.

Background of the Invention

Sphingosine-1-phosphate (S1P), a lipid metabolite, has been recognized and demonstrated as an important signaling mediator for vital cellular and physiological processes, such as cell motility, invasion, proliferation, angiogenesis and apoptosis. S1P is produced from sphingosine by two kinases, namely, sphingosine kinase 1 (SphK1) and sphingosine kinase 2 (SphK2). Upon production, S1P is secreted and interacts with a family of G-protein coupled receptors (S1P$_{1-5}$) on the cell surface to impart a plethora of roles in the regulation of diverse physiological functions such as inflammation, immunity and angiogenesis. Recently, intracellular targets, such as histone deacetylase (HDAC) and TRAF2, have been identified for S1P produced by SphK1 and SphK2, respectively, thus suggesting additional intracellular roles of this sphingolipid metabolite.

S1P and its biosynthetic precursors ceramide and sphingosine are the best characterized bioactive metabolites of sphingolipids. Ceramide and sphingosine have been associated with growth arrest and apoptosis. In contrast, S1P has been demonstrated to play important pro-survival roles. Therefore, the levels of these lipid metabolites need to be tightly controlled and a so called sphingolipid rheostat has been proposed to be crucial in determining cell fate. The regulation of the levels of these metabolites is complex and a number of enzymes have been demonstrated to play important roles, among which the SphKs have emerged as a central player in this complex system. SphKs are the key enzymes that catalyze the production of S1P. To date, two isoenzymes, SphK1 and SphK2 have been identified in human tissues. Although SphK1 and SphK2 share a high degree of homology, they have significant differences in size, tissue distribution, and subcellular localization, thus suggesting their distinct roles in regulation of different physiological functions. For example, SphK1 is mainly localized in the cytosol while SphK2 is present in several intracellular compartments, mainly in the nucleus, endoplasmic reticulum, and mitochondria. Evidence has accumulated that SphK1 promotes cell growth and survival while the function of SphK2 is complex and controversial. Consistent with this notion, numerous studies have shown that SphK1 is frequently up-regulated and overexpressed in tumor tissues compared to normal tissues and SphK1 has been associated with many aspects of cancer progression such as proliferation, migration, invasion and angiogenesis. SphK1/S1P has also been implicated in the pathology of asthma, inflammatory diseases and sepsis. Compared to SphK1, much less is known about SphK2 and the results are contrasting. Initially, SphK2 had been demonstrated to be pro-apoptotic. For example, overexpression of SphK2 suppresses growth and promotes apoptosis. However, it has also been demonstrated that downregulation of SphK2 inhibits the proliferation and migration of tumor cells such as glioblastoma and breast cancer cells. These controversial results strongly suggest developing powerful and selective pharmacological tools for SphK2 to better understand the roles of SphK2 in different pathological conditions. Even though a number of pan-SphK and selective SphK1 inhibitors have been developed and reported, the development of SphK2-selective inhibitors remains limited and SphK2 inhibitors remain scarce, with only a few SphK2 inhibitors having been reported in the literature (e.g. ABC294620, SG-12, R-FTY720-OMe and trans-12). Therefore, there is an urgent need to develop SphK2-selective inhibitors.

SUMMARY OF THE INVENTION

Development of isoform selective SphK inhibitors has attracted extensive attention as they may serve as valuable pharmacological tools to help decipher the physiological and pathological roles of SphKs and as effective therapeutic agents for human diseases, such as cancer. Even though several pan SphK inhibitors and SphK1 selective inhibitors have been developed and tested in preclinical experiments, selective SphK2 inhibitors remain scarce. During efforts to design and develop novel 5-alkylidene-thiazolidine-2,4-dione derivatives as dual-pathway inhibitors of the Raf/MEKIERK and PI3K/Akt signaling pathways, a family of 4-substituted-phenylpropylidene-thiazolidine-2,4-dione analogs were discovered to be highly selective SphK2 inhibitors. In addition, a series of 3-alkylidene-1,3-dihydro-indol-2-one analogs has been designed to replace the thiazolidine-2,4-dione heterocycle and they also function as selective SphK2 inhibitors. Thus, these compounds, depicted in generic Formula I and generic Formula II, are selective SphK2 inhibitors and represent novel therapeutic agents, such as anticancer agents. In the Formulas which are depicted herein, the letters N, V, W, X, Y and Z represent atoms in the structures of the compounds which may vary as described herein, and do not represent elements such a vanadium, tungsten, etc.

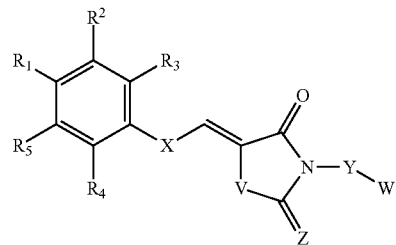

Formula I

-continued

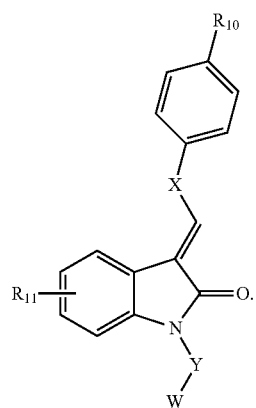

Formula II

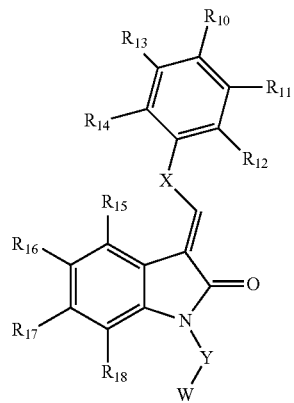

Formula II

It is an object of this invention to provide a compound of Formula I:

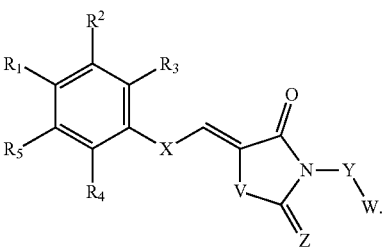

In Formula I, $R_1$ is selected from the group consisting of: $C_3$-$C_{14}$ alkyl and $C_3$-$C_{14}$ alkoxyl; $R_2$, $R_3$, $R_4$ and $R_5$ may be the same or different and are independently selected from: H, $C_1$-$C_8$ alkyl, $C_1$-$C_8$ alkoxyl, $C_1$-$C_8$ alkylcarbonyl, halogen, hydroxyl, amino, nitro, and cyano; V is S, O, NH, or $CH_2$; X is $C_1$-$C_4$ alkyl; Y is $C_1$-$C_4$ alkyl; Z is S or O or $NR^6$ in which $R^6$ is selected from the group consisting of: H, $C_1$-$C_8$ alkyl, or isopropyl, or tert-butyl, or a saturated or unsaturated monocyclic ring with ring size ranging from 3-7 carbons per ring, or unsubstituted or substituted phenyl ring which may be substituted with one or more substituents selected from the group consisting of: $C_1$-$C_8$ alkyl, $C_1$-$C_8$ alkoxyl, $C_1$-$C_8$ alkylcarbonyl, halogen, hydroxyl, amino, nitro, and cyano; W is $NR^{16}R^{17}$ where $R^{16}$ and $R^{17}$ may be the same or different and are H; $C_1$-$C_4$ alkyl; a saturated heterocycle comprising N bonded directly to Y; or an unsubstituted or substituted guanidine moiety.

It is also an object of this invention to provide a compound of Formula II:

wherein, $R_{10}$ is selected from the group consisting of: $C_3$-$C_{14}$ alkyl, $C_3$-$C_{14}$ alkoxyl; $R_{11}$, $R_{12}$, $R_{13}$ and $R_{14}$ may be the same or different and are independently selected from: H, $C_1$-$C_8$ alkyl, $C_1$-$C_8$ alkoxyl, $C_1$-$C_8$ alkylcarbonyl, halogen, hydroxyl, amino, nitro, and cyano; $R_{15}$, $R_{16}$, $R_{17}$ and $R_{18}$ may be the same or different and are independently selected from the group consisting of: H, $C_1$-$C_8$ alkyl, $C_1$-$C_8$ alkoxyl, $C_1$-$C_8$ alkylcarbonyl, halogen, hydroxyl, amino, nitro, and cyano; X is $C_1$-$C_4$ alkyl; Y is $C_1$-$C_4$ alkyl; and W is $NR^{16}R^{17}$ where $R^{16}$ and $R^{17}$ may be the same or different and are H; $C_1$-$C_4$ alkyl; a saturated heterocycle comprising N bonded directly to Y; or an unsubstituted or substituted guanidine moiety.

The invention also provides methods of treating cancer in a patient in need thereof. The method comprises the step of administering to the patient a sufficient quantity of a compound of at least one compound of Formula I:

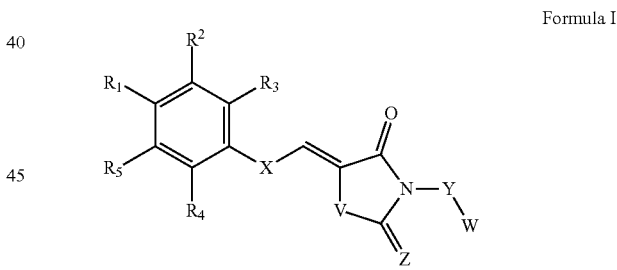

Formula I where, $R_1$ is selected from the group consisting of: $C_3$-$C_{14}$ alkyl and $C_3$-$C_{14}$ alkoxyl; $R_2$, $R_3$, $R_4$ and $R_5$ may be the same or different and are independently selected from: H, $C_1$-$C_8$ alkyl, $C_1$-$C_8$ alkoxyl, $C_1$-$C_8$ alkylcarbonyl, halogen, hydroxyl, amino, nitro, and cyano; V is S, O, NH, or $CH_2$; X is $C_1$-$C_4$ alkyl; Y is $C_1$-$C_4$ alkyl; Z is S or O or $NR^6$ in which $R^6$ is selected from the group consisting of: H, $C_1$-$C_8$ alkyl, or isopropyl, or tert-butyl, or a saturated or unsaturated monocyclic ring with ring size ranging from 3-7 carbons per ring, or unsubstituted or substituted phenyl ring which may be substituted with one or more substituents selected from the group consisting of: $C_1$-$C_8$ alkyl, $C_1$-$C_8$ alkoxyl, $C_1$-$C_8$ alkylcarbonyl, halogen, hydroxyl, amino, nitro, and cyano; and W is $NR^{16}R^{17}$ where $R^{16}$ and $R^{17}$ may be the same or different and are H; $C_1$-$C_4$ alkyl; a saturated heterocycle comprising N bonded directly to Y; or an unsubstituted or substituted guanidine moiety.

In one embodiment of the method, the number of carbon atoms in the alkoxyl substituent of $R_1$ is 4, 7, or 8. In other embodiments, W is $NH_2$. The compound may be, for example, 3-(2-aminoethyl)-5-[3-(4-butoxyl-phenyl)-propylidene]-thiazolidine-2,4-dione (Formula III, also referred to herein as "K145" or "compound (30)") or 3-(2-aminoethyl)-5-[3-(4-octoxy-phenyl)-propylidene]-thiazolidine-2,4-dione (Formula IV, also referred to herein as "KL11116" or "KL111016" or "compound (31)").

Formula III

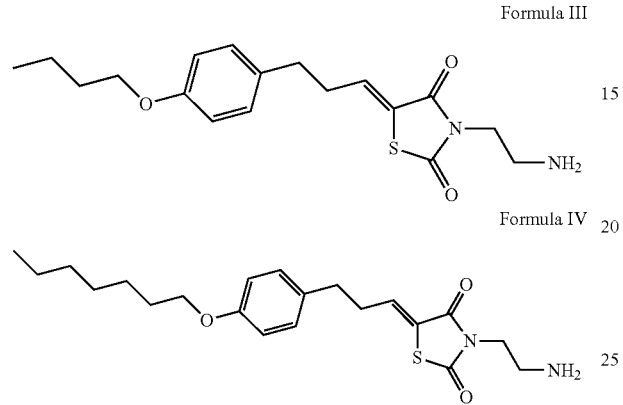

Formula IV

The invention also provides methods of treating cancer in a patient in need thereof. The method comprises the step of administering to the patient a quantity of at least one compound of Formula II sufficient to cure or ameliorate cancer symptoms:

Formula II

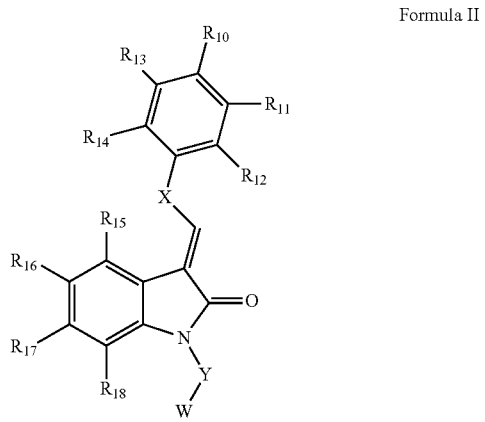

where, $R_{10}$ is selected from the group consisting of: $C_3$-$C_{14}$ alkyl, $C_3$-$C_{14}$ alkoxyl; $R_{11}$, $R_{12}$, $R_{13}$ and $R_{14}$ may be the same or different and are independently selected from: H, $C_1$-$C_8$ alkyl, $C_1$-$C_8$ alkoxyl, $C_1$-$C_8$ alkylcarbonyl, halogen, hydroxyl, amino, nitro, and cyano; $R_{15}$, $R_{16}$, $R_{17}$ and $R_{18}$ may be the same or different and are independently selected from the group consisting of: H, $C_1$-$C_8$ alkyl, $C_1$-$C_8$ alkoxyl, $C_1$-$C_8$ alkylcarbonyl, halogen, hydroxyl, amino, nitro, and cyano; X is $C_1$-$C_4$ alkyl; Y is $C_1$-$C_4$ alkyl; and W is $NR^{16}R^{17}$ where $R^{16}$ and $R^{17}$ may be the same or different and are H; $C_1$-$C_4$ alkyl; a saturated heterocycle comprising N bonded directly to Y; or an unsubstituted or substituted guanidine moiety.

The invention further provides a method of inhibiting the growth or killing or damaging of human cancer cells. The method comprises the step of exposing the cell to at least one compound of Formula I and/or Formula II:

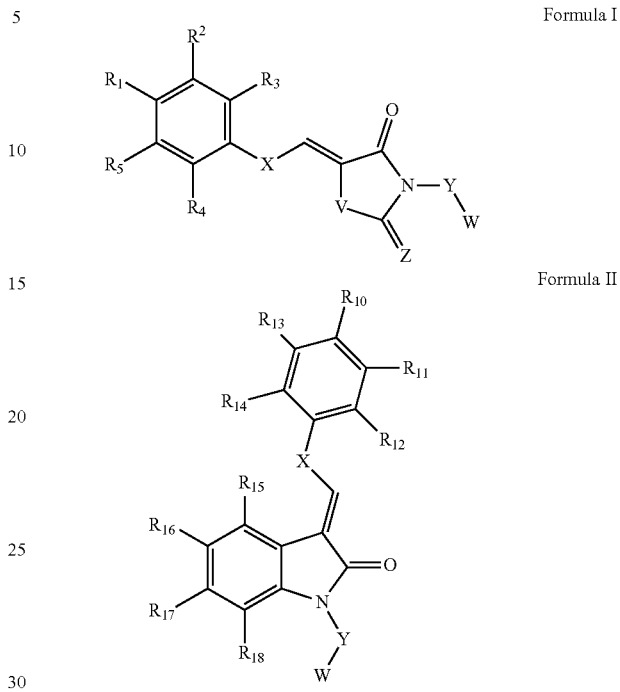

In Formula I, $R_1$ is selected from the group consisting of: $C_3$-$C_{14}$ alkyl and $C_3$-$C_{14}$ alkoxyl; $R_2$, $R_3$, $R_4$ and $R_5$ may be the same or different and are independently selected from: H, $C_1$-$C_8$ alkyl, $C_1$-$C_8$ alkoxyl, $C_1$-$C_8$ alkylcarbonyl, halogen, hydroxyl, amino, nitro, and cyano; V is S, O, NH, or $CH_2$; X is $C_1$-$C_4$ alkyl; Y is $C_1$-$C_4$ alkyl; Z is S or O or $NR^6$ in which $R^6$ is selected from the group consisting of: H, $C_1$-$C_8$ alkyl, or isopropyl, or tert-butyl, or a saturated or unsaturated monocyclic ring with ring size ranging from 3-7 carbons per ring, or unsubstituted or substituted phenyl ring which may be substituted with one or more substituents selected from the group consisting of: $C_1$-$C_8$ alkyl, $C_1$-$C_8$ alkoxyl, $C_1$-$C_8$ alkylcarbonyl, halogen, hydroxyl, amino, nitro, and cyano; and W is $NR^{16}R^{17}$ where $R^{16}$ and $R^{17}$ may be the same or different and are H; $C_1$-$C_4$ alkyl; a saturated heterocycle comprising N bonded directly to Y; or an unsubstituted or substituted guanidine moiety.

In Formula II, $R_{10}$ is selected from the group consisting of: $C_3$-$C_{14}$ alkyl, $C_3$-$C_{14}$ alkoxyl; $R_{11}$, $R_{12}$, $R_{13}$ and $R_{14}$ may be the same or different and are independently selected from: H, $C_1$-$C_8$ alkyl, $C_1$-$C_8$ alkoxyl, $C_1$-$C_8$ alkylcarbonyl, halogen, hydroxyl, amino, nitro, and cyano; $R_{15}$, $R_{16}$, $R_{17}$ and $R_{18}$ may be the same or different and are independently selected from the group consisting of: H, $C_1$-$C_8$ alkyl, $C_1$-$C_8$ alkoxyl, $C_1$-$C_8$ alkylcarbonyl, halogen, hydroxyl, amino, nitro, and cyano; X is $C_1$-$C_4$ alkyl; Y is $C_1$-$C_4$ alkyl; and W is $NR^{16}R^{17}$ where $R^{16}$ and $R^{17}$ may be the same or different and are H; $C_1$-$C_4$ alkyl; a saturated heterocycle comprising N bonded directly to Y; or an unsubstituted or substituted guanidine moiety.

In one embodiment of the method, the number of carbon atoms in the alkoxyl substituent of $R_1$ is 4, 7, or 8. In other embodiments, W is $NH_2$. The compound may be, for example, 3-(2-aminoethyl)-5-[3-(4-butoxyl-phenyl)-propylidene]-thiazolidine-2,4-dione (Formula III) or 3-(2-aminoethyl)-5-[3-(4-octoxy-phenyl)-propylidene]-thiazolidine-2,4-dione (Formula IV).

In yet another embodiment of the method, the cell that is exposed to the compound is a cancer cell. In some embodiments, the cancer cells are leukemia, lymphoma, sarcoma, neuroblastoma, lung cancer, skin cancer, head squamous cell carcinoma, neck squamous cell carcinoma, prostate cancer, colon cancer, breast cancer, ovarian cancer, cervical cancer, brain cancer, bladder cancer, and/or pancreatic cancer cells.

The invention also provides a method of inhibiting SphK2. The method comprises the step of exposing the kinase enzyme to a compound of Formula I or Formula II:

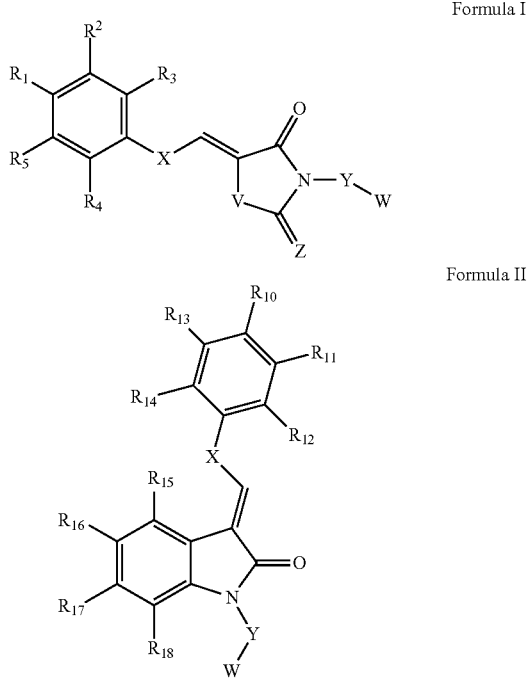

Formula I

Formula II

In Formula I, $R_1$ is selected from the group consisting of: $C_3$-$C_{14}$ alkyl and $C_3$-$C_{14}$ alkoxyl; $R_2$, $R_3$, $R_4$ and $R_5$ may be the same or different and are independently selected from: H, $C_1$-$C_8$ alkyl, $C_1$-$C_8$ alkoxyl, $C_1$-$C_8$ alkylcarbonyl, halogen, hydroxyl, amino, nitro, and cyano; V is S, O, NH, or $CH_2$; X is $C_1$-$C_4$ alkyl; Y is $C_1$-$C_4$ alkyl; Z is S or O or $NR^6$ in which $R^6$ is selected from the group consisting of: H, $C_1$-$C_8$ alkyl, or isopropyl, or tert-butyl, or a saturated or unsaturated monocyclic ring with ring size ranging from 3-7 carbons per ring, or unsubstituted or substituted phenyl ring which may be substituted with one or more substituents selected from the group consisting of: $C_1$-$C_8$ alkyl, $C_1$-$C_8$ alkoxyl, $C_1$-$C_8$ alkylcarbonyl, halogen, hydroxyl, amino, nitro, and cyano; and W is $NR^{16}R^{17}$ where $R^{16}$ and $R^{17}$ may be the same or different and are H; $C_1$-$C_4$ alkyl; a saturated heterocycle comprising N bonded directly to Y; or an unsubstituted or substituted guanidine moiety.

In Formula II, $R_{10}$ is selected from the group consisting of: $C_3$-$C_{14}$ alkyl, $C_3$-$C_{14}$ alkoxyl; $R_{11}$, $R_{12}$, $R_{13}$ and $R_{14}$ may be the same or different and are independently selected from: H, $C_1$-$C_8$ alkyl, $C_1$-$C_8$ alkoxyl, $C_1$-$C_8$ alkylcarbonyl, halogen, hydroxyl, amino, nitro, and cyano; $R_{15}$, $R_{16}$, $R_{17}$ and $R_{18}$ may be the same or different and are independently selected from the group consisting of: H, $C_1$-$C_8$ alkyl, $C_1$-$C_8$ alkoxyl, $C_1$-$C_8$ alkylcarbonyl, halogen, hydroxyl, amino, nitro, and cyano; X is $C_1$-$C_4$ alkyl; Y is $C_1$-$C_4$ alkyl; and W is $NR^{16}R^{17}$ where $R^{16}$ and $R^{17}$ may be the same or different and are H; $C_1$-$C_4$ alkyl; a saturated heterocycle comprising N bonded directly to Y; or an unsubstituted or substituted guanidine moiety.

In one embodiment of the method, the number of carbon atoms in the alkoxyl substituent of $R_1$ is 4, 7, or 8. In other embodiments, W is $NH_2$. The compound may be, for example, 3-(2-aminoethyl)-5-[3-(4-butoxyl-phenyl)-propylidene]-thiazolidine-2,4-dione (Formula III) or 3-(2-aminoethyl)-5-[3-(4-octoxy-phenyl)-propylidene]-thiazolidine-2,4-dione (Formula IV).

BRIEF DESCRIPTION OF THE DRAWINGS

FIG. 13A-D. K145 suppresses the growth of U937 xenograft in nude mice. BALB/c-nu mice (n=7) with palpable U937 xenograft were treated daily with vehicle, tamibarotene (15 mg/kg), or K145 (15 mg/kg) for 17 days by i.p. injection. A) After treatment, animals were sacrificed and tumors were removed and weighed and the TGI was calculated; B) Tumor volumes were measured every other day during the treatment course; C) Animal weights were measured every other day during treatment course. D) Body weights of mice throughout treatment. Data are expressed as mean value±SD. *P<0.05 compared to control group.

FIG. 14A-E. K145 suppresses the growth of JC xenograft in BALB/c mice. BALB/c mice (n=8) with palpable JC xenograft were treated daily with vehicle or K145 (20 mg/kg and 35 mg/kg) for 15 days by i.p. injection. A) Tumor volumes were measured every other day; B) After treatment, animals were sacrificed and tumors were removed and weighed; C) The S1P and K145 levels in the tumor samples from vehicle and treatment (20 mg/kg) groups (n=4) were measured by ESI-MS/MS; D) Images of tumor samples from control and treatment groups (n=7 for each group) after the experiments; E) Tumor samples (20 mg/kg and control groups) were analyzed by Western blot. Data are expressed as mean value±SEM. *P<0.05 compared to control group.

FIG. 15A-D. K145 suppresses the growth of U937 tumors in nude mice by oral administration. BALB/c-nu mice (n=7) with palpable U937 xenograft were treated daily with vehicle, tamibarotene (20 mg/kg), or K145 (50 mg/kg) for 15 days by oral gavage. After treatment, animals were sacrificed and tumors were removed, weighed and images were taken. A) Tumor weight and TGI comparison; B) Images of tumor samples from control and treatment groups (n=7 for each group) after the experiments; C) Tumor volumes were measured every other day; D) Animal weights were measured every other day. Data are expressed as mean value±SEM. *P<0.05 compared to control group.

FIG. 16A-E. K145 accumulates and suppresses the S1P level. A and B) U937 cells were treated with K145 at the indicated concentrations for 3 h and the levels of K145 and S1P were measured by ESI-MS/MS. C) HEK293 cells were treated with K145 (10 μM) for 2 h. Lipids were extracted and different chain length species of ceramide were determined by LC-ESI-MS/MS. Numbers indicate chain length followed by the number of double bonds in the fatty acid. Data are averages of triplicate determinations and are expressed as pmol lipid/$10^6$ cells. D) U937 cells were treated with or without K145 (10 μM) for 3 h and levels of C1P species were determined by ESI-MS/MS. E) U937 cells were treated with FTY720 (1 μM) in the absence or presence of indicated K145 for 3 h, then FTY720-P was measured by ESI-MS/MS. *P<0.05 compared to control.

DETAILED DESCRIPTION

Figure 1B:
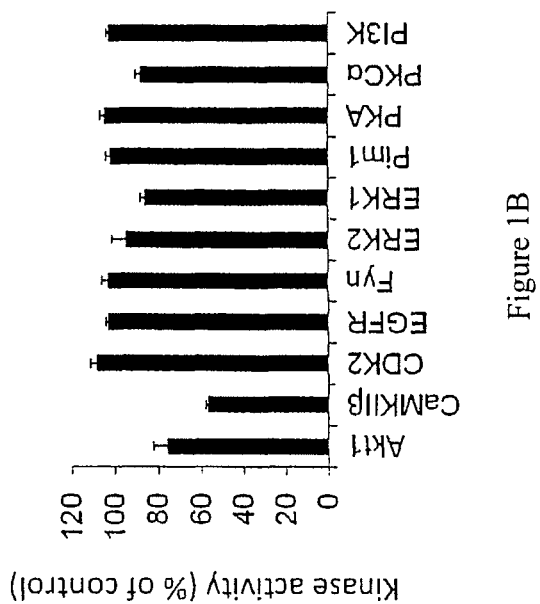
FIG. 1A-B. K145 inhibits SphK2 but not SphK1. A) SphK1 and SphK2 activities were measured with 5 µM sphingosine in the absence or presence of the indicated concentrations of K145 or 10 µM DMS. Data are expressed as percentage SphK activity in the absence of inhibitor; B) Effect of K145 (10 µM) on activity of the indicated enzymes was tested by SelectScreen Kinase Profiling from Invitrogen. CaMK11β, Ca2+/calmodulin-dependent protein kinase II; CDK2, cyclin-dependent kinase 2; EGFR, Epidermal Growth Factor Receptor; Fyn, Fyn Kinase (p55); ERK2, extracellular signal-regulated kinase 2; ERK1, extracellular signal-regulated kinase 1; PKA, protein kinase A; PKCα, protein kinase C α; P13K, phosphatidylinositide 3-kinase. Data are expressed as percentage of control activity averaged from 2 independent experiments. Data are expressed as mean value±SEM.

The invention provides compounds of the following Formula I and Formula II:

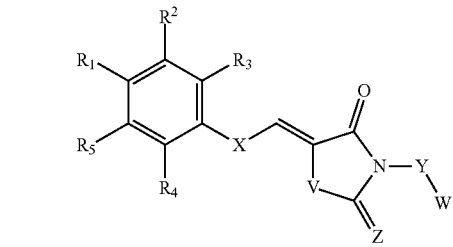

Formula I

In Formula I:
$R_1$ is selected from the group consisting of: $C_3$-$C_{14}$ alkyl and $C_3$-$C_{14}$ alkoxyl;
$R_2$, $R_3$, $R_4$ and $R_5$ may be the same or different and are independently selected from: H, $C_1$-$C_8$ alkyl, $C_1$-$C_8$ alkoxyl, $C_1$-$C_8$ alkylcarbonyl, halogen, hydroxyl, amino, nitro, and cyano;
V is S, O, NH, or $CH_2$;
X is $C_1$-$C_1$ alkyl;
Y is $C_1$-$C_4$ alkyl;
Z is S or O or $NR^6$ in which $R^6$ is selected from the group consisting of: H, $C_1$-$C_8$ alkyl, or isopropyl, or tert-butyl, a saturated or unsaturated monocyclic ring with ring size ranging from 3-7 carbons per ring, an unsubstituted or substituted phenyl ring which may be substituted with one or more substituents selected from the group consisting of: $C_1$-$C_8$ alkyl, $C_1$-$C_8$ alkoxyl, $C_1$-$C_8$ alkylcarbonyl, halogen, hydroxyl, amino, nitro, and cyano; and
W is $NR_7R_8$ where $R_7$ and $R_8$ may be the same or different and are independently selected from H; $C_1$-$C_4$ alkyl; a saturated heterocycle comprising N bonded directly to Y; and an unsubstituted or substituted guanidine moiety.

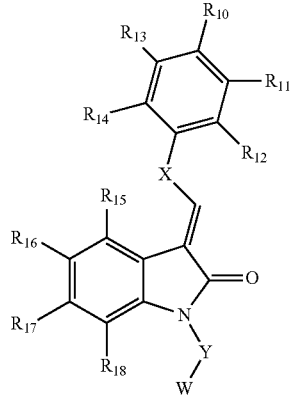

Formula II

In Formula II:
$R_{10}$ is selected from the group consisting of: $C_3$-$C_{14}$ alkyl, $C_3$-$C_{14}$ alkoxyl;
$R_{11}$, $R_{12}$, $R_{13}$ and $R_{14}$ may be the same or different and are independently selected from: H, $C_1$-$C_8$ alkyl, $C_1$-$C_8$ alkoxyl, $C_1$-$C_8$ alkylcarbonyl, halogen, hydroxyl, amino, nitro, and cyano;
$R_{15}$, $R_{16}$, $R_{17}$ and $R_{18}$ may be the same or different and are independently selected from the group consisting of: H, $C_1$-$C_8$ alkyl, $C_1$-$C_8$ alkoxyl, $C_1$-$C_8$ alkylcarbonyl, halogen, hydroxyl, amino, nitro, and cyano;
X is $C_1$-$C_4$ alkyl;
Y is $C_1$-$C_4$ alkyl;

and

W is $NR^{16}R^{17}$ where $R^{16}$ and $R^{17}$ may be the same or different and are H; $C_1$-$C_4$ alkyl; a saturated heterocycle comprising N bonded directly to Y; or an unsubstituted or substituted guanidine moiety.

By "saturated heterocycle" we mean a saturated monocyclic carbon ring containing at least one heteroatom atom N as part of the ring. The monocyclic ring is fully saturated (i.e. it does not contain any carbon-carbon double or triple bonds). In addition to N bonded directly to Y, one or more additional positions in the ring(s) may be substituted by other heteroatoms, examples of which include but are not limited to: N, O, S, etc. Exemplary saturated heterocycles that may be used in the practice of the invention include but are not limited to morpholine, pipieridine, piperazine, pyrrolidine, etc.

By "saturated or unsaturated monocyclic ring" we mean a fully saturated monocyclic carbon ring (i.e. it does not contain any carbon-carbon double or triple bonds) without or with at least one heteroatom, examples of which include but are not limited to: one or more N, O, S, etc; as part of the ring. Unsaturated monocyclic ring means a monocyclic carbon ring containing one or more carbon-carbon or carbon-heteroatom double or triple bonds) without or with at least one heteroatom, examples of which include but are not limited to: one ore more N, O, S, etc; as part of the ring.

$C_1$-$C_4$ alkyl includes include substituents with 1, 2, 3, or 4 carbon atoms and may be unbranched or branched isomeric forms thereof, e.g. methyl, ethyl, propyl, isopropyl, butyl, isobutyl, sec-butyl, tert-butyl; $C_1$-$C_8$ alkyl, $C_1$-$C_8$ alkoxyl, and $C_1$-$C_8$ alkylcarbonyl include substitutents with 1, 2, 3, 4, 5, 6, 7, or 8 carbon atoms in the alkyl portion of the molecule (which may be unbranched or branched isomeric forms thereof), e.g. they comprise methyl, ethyl, propyl, isopropyl, butyl, isobutyl, sec-butyl, tert-butyl, pentyl, isopentyl, neopentyl, hexyl, 2-methylpentane, 3-methylpentane, 2,3-dimethylbutane, 2,2-dimethylbutane and various 8-carbon octyl component and branched isomers thereof, etc., as understood in the art.

In one embodiment of the invention, the compound of Formula I is the compound 3-(2-aminoethyl)-5-[3-(4-butoxyl-phenyl)-propylidene]-thiazolidine-2,4-dione shown in Formula III. In another embodiment of the invention, the compound of Formula I is 3-(2-aminoethyl)-5-[3-(4-octoxyphenyl)-propylidene]-thiazolidine-2,4-dione shown in Formula IV. The compounds of Formulas III and IV inhibit SphK2 selectively, i.e. they do not inhibit SphK1, or they inhibit SphK2 to a greater extent, e.g. inhibition of SphK2 is at least about 2 fold, and usually about 5, 10, 20, 30, 40, 50, 60, 70, 80, 90 or 100-fold or more greater than is inhibition of SphK1.

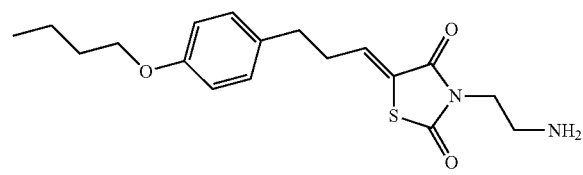

Formula III

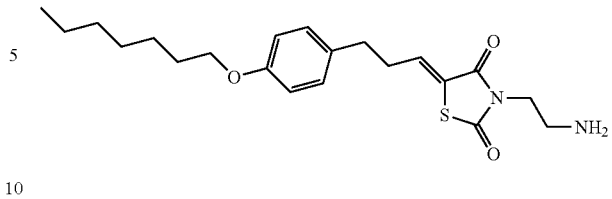

Formula IV

The synthesis and structural characterization of the compounds represented by Formula III and Formula IV are described in Examples 3, 10 and 15.

Figure 3:
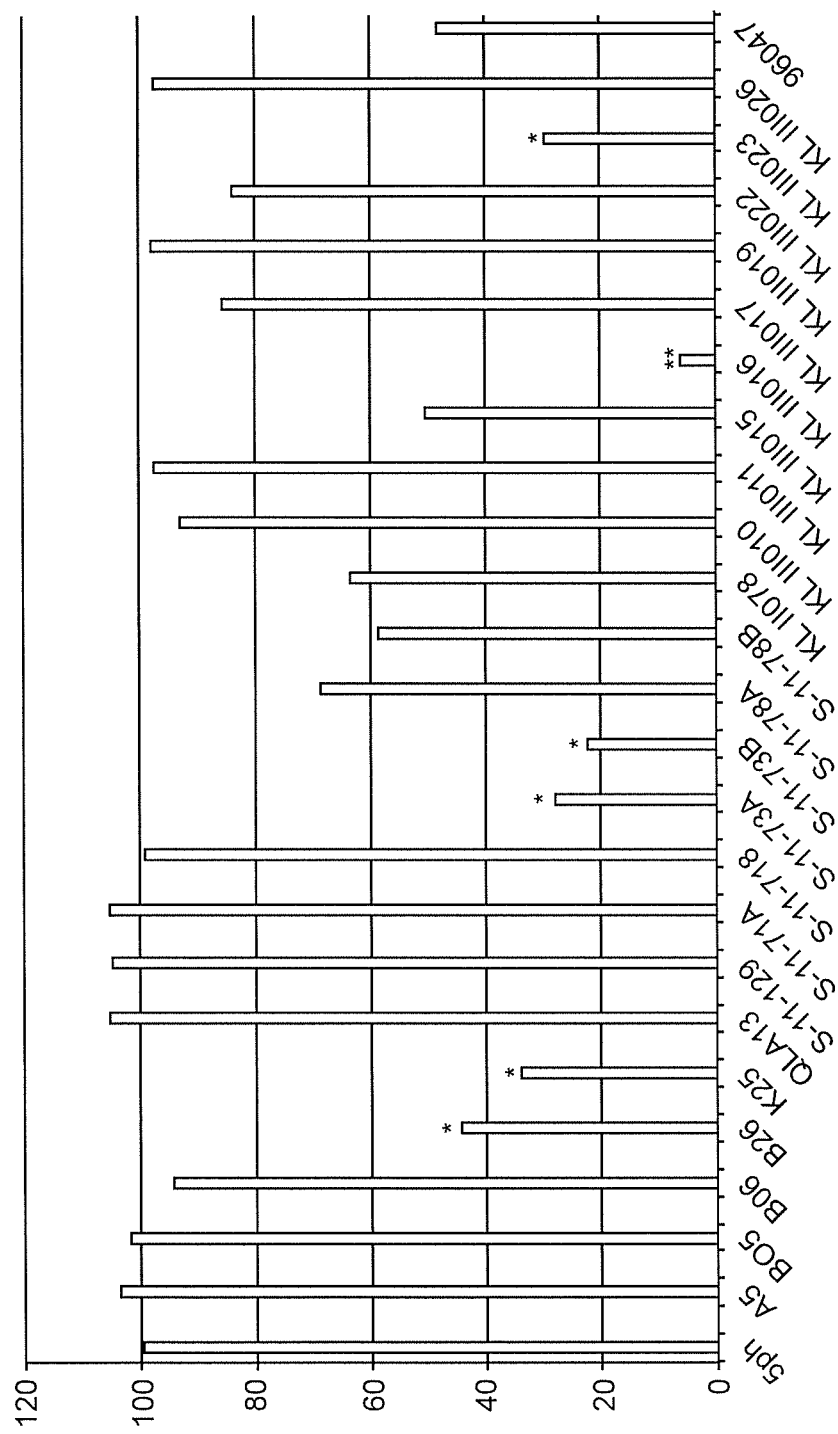
FIG. 3. SphK2 was incubated with indicated compounds at 10 µM, then the activity of SphK2 was determined. The data shown here is a relative activity of SphK2 compared to control (no inhibitor, column labeled Sph in the Figure). 96047 is a known SpK2 inhibitor. A5, B26, K25 and QLA13 are known compounds [Li et al. (2009) Bioorg Med Chem Lett 19: 6042-6046; Liu et al. (2012) Eur J Med Chem 47: 125-137] and were tested for purposes of comparison. "A" and "B" refer to different batches of a compound.
Figure 4:
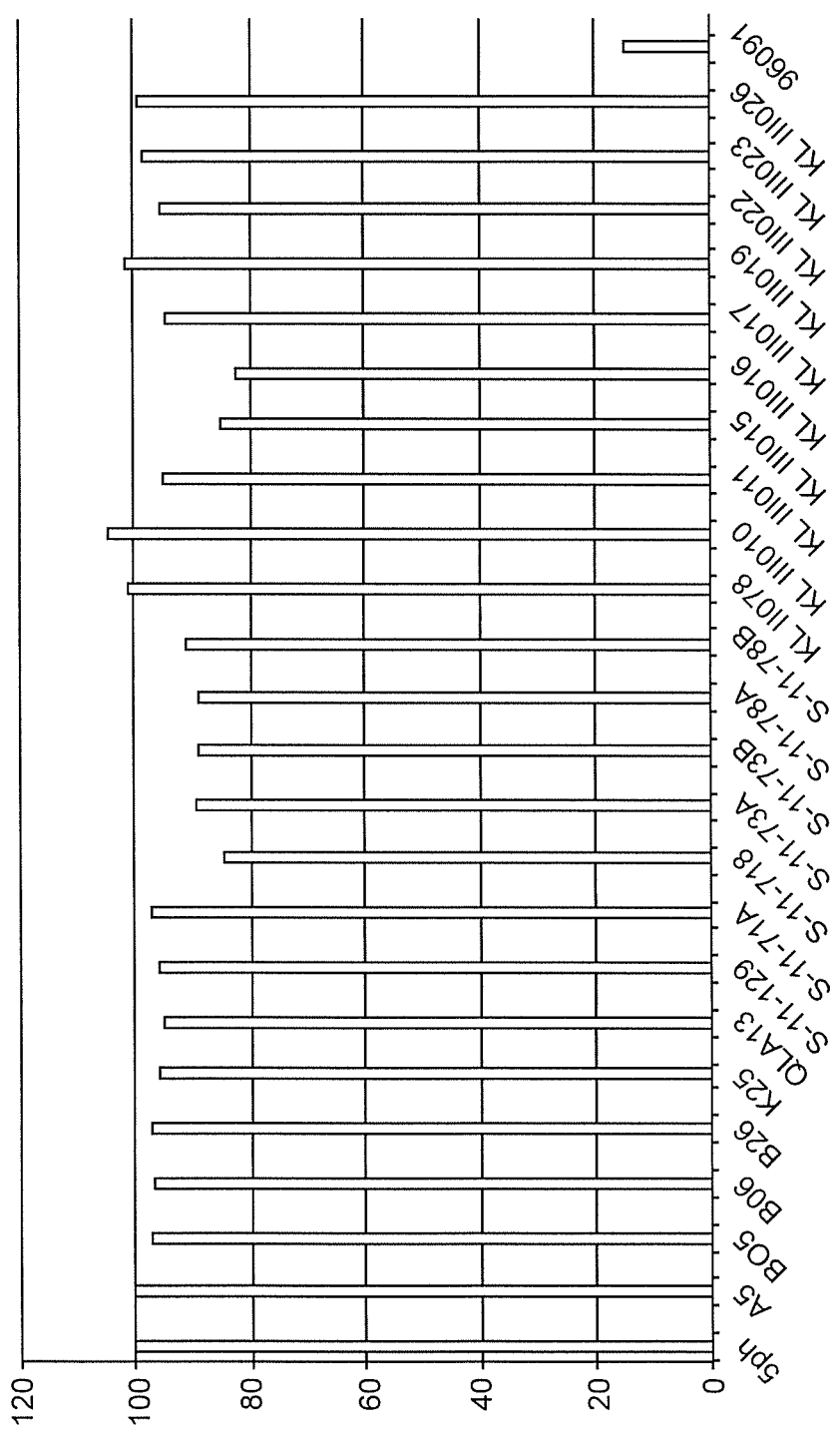
FIG. 4. SphK1 was incubated with indicated compounds at 10 µM, then the activity of SphK1 was determined. The data shown here is a relative activity of SphK1 compared to control (no inhibitor, column labeled Sph in the Figure). 96091 is a known Spk1 inhibitor. A5, B26, K25 and QLA13 are as above for FIG. 4. "A" and "B" refer to different batches of a compound.

Other compounds that inhibited SphK2 include: S-11-73, compound (61); KL11016, compound (31); and KL111023, compound (33); (see FIGS. 3 and 4 for activity and Example 8 for structures of (61), (31), (33); and KL11139, compound (34)]; KL1147, compound (35); KL157, compound (32); S-11-103, compound (66); and S-11-104, compound (70); (see FIGS. 5 and 6 for activity and Example 8 for structures of (34), (35), (32), (66), (70)). These compounds inhibited SphK2 selectively, compared to Sphk1, i.e. they did not inhibit SphK1 or inhibited SphK1 to a lesser extent as described above.

Figure 5:
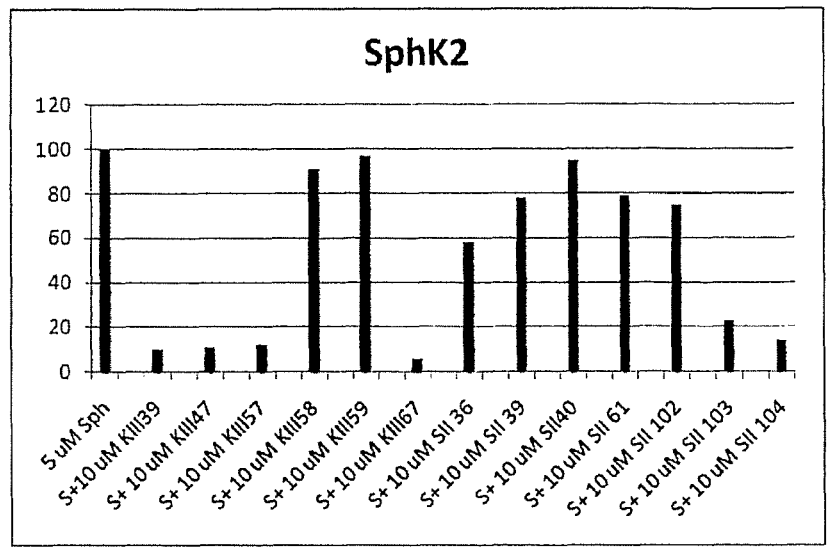
FIG. 5. SphK2 was incubated with indicated compounds at 10 µM, then the activity of SphK2 was determined. The data shown here is a relative activity of SphK2 compared to control (no inhibitor).
Figure 6:
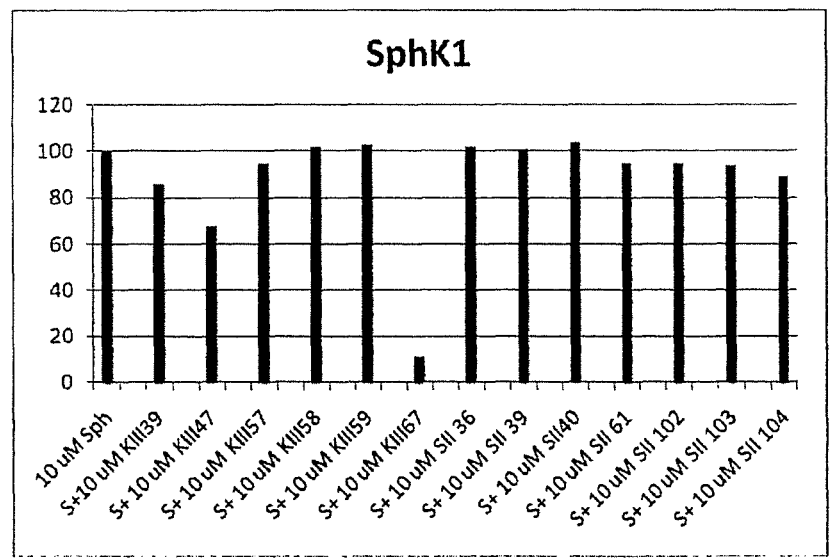
FIG. 6. SphK1 was incubated with indicated compounds at 10 µM, then the activity of SphK2 was determined. The data shown here is a relative activity of SphK2 compared to control (no inhibitor).

Compound K11167 [compound (42) herein] inhibits both Sphk1 and Sphk2 (see FIGS. 5 and 6 for activity and Example 8 for the structure of compound (42)), and may be used for the non-selective inhibition of one or both of the enzymes.

The invention also provides compositions for the treatment of diseases or conditions associated with the over-activation or over-expression of SphK2. In particular, the invention provides compositions for the treatment of various cancers. The compositions comprise at least one compound of Formula I and/or at least one compound of Formula II and a pharmaceutically acceptable (i.e. a physiologically compatible) carrier, e.g. saline, pH in the range of about 6.5 to about 7.5, and usually about 7.2). Depending on the route of administration, the compositions can take the form of liquids suitable for injection or intravenous administration, aerosols, cachets, capsules, creams, elixirs, emulsions, foams, gels, granules, inhalants, liposomes, lotions, magmas, microemulsion, microparticles, ointments, peroral solids, powders, sprays, syrups, suppositories, suspensions, tablets and tinctures. The amount of the compound of Formula 1 and/or Formula II present in the composition can vary, but us usually in the range of from about 1 to 99%.

The compositions may include one or more pharmaceutically compatible additives or excipients. Commonly used pharmaceutical additives and excipients which can be used as appropriate to formulate the composition for its intended route of administration include but are not limited to:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC$—$CClF_2$ and $CClF_3$);

air displacement agents (examples include but are not limited to nitrogen and argon);

antifungal preservatives (examples include but are not limited to benzoic acid, butylparaben, ethylparaben, methylparaben, propylparaben, sodium benzoate, propionic acids or its salts);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite, tocopherol, and vitamin E);

binding materials (examples include but are not limited to block polymers, natural and synthetic rubber, polyacrylates, polyurethanes, silicones and styrene-butadiene copolymers);

buffering agents (examples include but are not limited to potassium metaphosphate, potassium phosphate monobasic, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid); colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel, ferric oxide red, natural colorants such as bixin, norbixin, and carmine);

clarifying agents (examples include but are not limited to bentonite);

emulsifying agents (examples include but are not limited to acacia, cetomacrogol, cetyl alcohol, glyceryl monostearate, lecithin, sorbitan monooleate, and polyethylene 50 stearate);

encapsulating agents (examples include but are not limited to gelatin and cellulose acetate phthalate);

fillers (examples include but are not limited to sugars, lactose, sucrose, sorbitol, cellulose preparations, calcium phosphates, natural or synthetic gums, solid starch, and starch pastes); flavorants (examples include but are not limited to anise oil, cinnamon oil, cocoa, menthol, orange oil, peppermint oil and vanillin);

humectants (examples include but are not limited to glycerin, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

plasticizers (examples include but are not limited to diethyl phthalate and glycerin);

solvents (examples include but are not limited to alcohol, corn oil, cottonseed oil, glycerin, isopropyl alcohol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (PEGS) (and mixtures containing one or both of cocoa butter and PEGs));

surfactants (examples include but are not limited to benzalkonium chloride, nonoxynol 10, oxtoxynol 9, polysorbate 80, sodium lauryl sulfate and sorbitan monopalmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, fructose, glycerin, mannitol, propylene glycol, saccharin sodium, sorbitol and sucrose);

tablet anti-adherents (examples include but are not limited to magnesium stearate and talc); tablet binders (examples include but are not limited to acacia, alginic acid, carboxymethylcellulose sodium, compressible sugar, ethylcellulose, gelatin, liquid glucose, methylcellulose, povidone and pregelatinized starch);

tablet and capsule diluents (examples include but are not limited to dibasic calcium phosphate, kaolin, lactose, mannitol, microcrystalline cellulose, powedered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide); tablet polishing agents (examples include but are not limited to carnuba wax and white wax);

thickening agents (examples include but are not limited to beewax, cetyl alcohol and paraffin);

tonicity agents (examples include but are not limited to dextrose and sodium chloride); viscosity increasing agents (examples include but are not limited to alginic acid, bentonite, carbomers, carboxymethylcellulose sodium, methylcellulose, povidone, sodium alginate and tragacanth); and wetting agents (examples include but are not limited to heptadecaethylene oxycetanol, lecithins, polyethylene sorbitol monooleate, polyoxyethylene sorbitol monooleate, polyoxyethylene stearate).

Additional additives and excipients suitable for pharmaceutical use such as those described in Remington's The Science and Practice of Pharmacy, 21$^{St}$ Edition (2005), Goodman & Gilman's The Pharmacological Basis of Therapeutics, 11$^{th}$ Edition (2005) and Ansel's Parmaceutical Dosage Forms and Drug Delivery Systems (8$^{th}$ Edition), edited by Allen et al., Lippincott Williams & Wilkins, (2005) are also considered to be within the scope of the invention. The complete contents of these references are herein incorporated by reference in entirety.

In one embodiment of the compositions of the invention, one or more (i.e. at least one) additional anti-cancer agent can be added to the composition. Representative anti-cancer agents include, but are not limited to, Erbitux, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel, γ-radiation, alkylating agents including nitrogen mustard such as cyclophosphamide, ifosfamide, trofosfamide, chlorambucil, nitrosoureas such as carmustine (BCNU), and lomustine (CCNU), alkylsulphonates such as busulfan, and treosulfan, triazenes such as dacarbazine, platinum containing compounds such as cisplatin and carboplatin, plant alkaloids including vinca alkaloids, vincristine, vinblastine, vindesine, and vinorelbine, taxoids including paclitaxel, and docetaxol, DNA topoisomerase inhibitors including epipodophyllins such as etoposide, teniposide, topotecan, 9-aminocamptothecin, campto irinotecan, and crisnatol, mitomycins such as mitomycin C, anti-metabolites, including anti-folates such as DHFR inhibitors, methotrexate and trimetrexate, IMP dehydrogenase inhibitors including mycophenolic acid, tiazofurin, ribavirin, EICAR, ribonucleotide reductase inhibitors such as hydroxyurea, deferoxamine, pyrimidine analogs including uracil analogs 5-fluorouracil, floxuridine, doxifluridine, and ratitrexed, cytosine analogs such as cytarabine (ara C), cytosine arabinoside, and fludarabine, purine analogs such as mercaptopurine, thioguanine, hormonal therapies including receptor antagonists, the anti-estrogens tamoxifen, raloxifene and megestrol, LHRH agonists such as goscrclin, and leuprolide acetate, anti-androgens such as flutamide, and bicalutamide, retinoids/deltoids, Vitamin D3 analogs including EB 1089, CB 1093, and KH 1060, photodyamic therapies including vertoporfin (BPD-MA), phthalocyanine, photosensitizer Pc4, Demethoxy-hypocrellin A, (2BA-2-DMHA), cytokines including Interferon, α-Interferon, γ-interferon, tumor necrosis factor, as well as other compounds having anti-tumor activity including isoprenylation inhibitors such as lovastatin, dopaminergic neurotoxins such as 1-methyl-4-phenylpyridinium ion, cell cycle inhibitors such as staurosporine, alsterpaullone, butyrolactone I, Cdk2 inhibitor, Cdk2/Cyclin Inhibitory Peptide I, Cdk2/Cyclin Inhibitory Peptide II, Compound 52 [2-(2-hydroxyethylamino)-6-(3-chloroanilino)-9-isopropylpurine], Indirubin-3'-monoxime, Kenpaullone, Olomoucine, Iso-olomoucine, N$^9$-isopropyl-olomoucine, Purvalanol A, Roscovitine, (S)-isomer Roscovitine and WHI-P180 [4-(3'-hydroxyphenyl)amino-6,7-dimethoxyquinazoline, actinomycins such as actinomycin D and dactinomycin, bleomycins such as bleomycin A2, bleomycin B2, and peplomycin, anthracyclines such as daunorubicin, doxorubicin (adriamycin), idarubicin, epirubicin, pirarubicin, zorubicin, and mitoxantrone, MDR inhibitors including verapamil, and Ca$^{2+}$ ATPase inhibitors such as thapsigargin.

In addition, the compounds or compositions of the invention may be administered in conjunction with other health-related and/or cancer treating substances or protocols, including but not limited to: dietary modifications (e.g. vitamin or antioxidant therapy); pain medication or procedures to lessen pain; radiation; various forms of chemotherapy (e.g. administration of platinum drugs, etc.; surgery; cryotherapy; and medications to lessen nausea, etc.).

The invention also provides methods of treating cancer in a patient in need thereof. The methods comprise a step of administering, to the patient, an effective amount of one or more compounds of Formulas I and/or II, e.g. as a composition comprising the compound(s). Methods of administration include but are not limited to intradermal, intramuscular, intraperitoneal, intravenous (IV), intratumoral, subcutaneous, intranasal, epidural, oral, sublingual, intranasal, intracerebral, intravaginal, transdermal, rectally, by inhalation, or topically, particularly to the ears, nose, eyes, or skin. Frequently, administration will be IV, although the mode of administration is left to the discretion of the skilled practitioner (e.g. a physician). In most instances, administration will result in the release of a compound of the invention into the bloodstream. However, this need not always be the case, e.g. with topical or intratumoral administration. Further, modes of administration may be combined, e.g. intravenous and intratumoral administration may both be carried out in a patient.

The amount of the compound(s) of Formulas I and/or II that is administered in one administration is generally in the range of from about 0.1 to about 10 mg/kg of body weight of the patient, and is usually in the range of from about 0.1 to about 10 mg/kg, with a goal of achieving levels of from about 1 to about 5 µM in the blood stream. Those of skill in the art will recognize that administration may be carried out according to any of several protocols, and will generally be determined by a skilled practitioner such as a physician. For example, administration may be once per day, several times per day, or less frequent (e.g. weekly, biweekly, etc.). The amount of the compound that is administered and the frequency of administration may depend on several factors, e.g. the characteristics of the patient (weight, age, gender, overall state of health, etc.); the type and stage of the cancer being treated; the response of the patient to the treatment; etc.

By "an effective amount" we mean an amount that is sufficient to ameliorate, lessen or eliminate symptoms of the disease that is being treated. While in some cases, the patient may be completely "cured" (disease symptoms disappear entirely), this need not always be the case. Those of skill in the art will recognize that substantial benefits may accrue if disease symptoms are only partially mitigated, or if the progress of the disease is slowed. For example, when treating cancer, substantial benefits re quality of life and longevity are obtained by slowing or arresting the growth of a tumor and/or preventing metastasis, shrinking (decreasing) the size of a tumor, etc. even if the tumor itself is not entirely destroyed by exposure to the compounds described herein. In some cases, the cancer cells which are exposed to the compounds of the invention are killed; in other embodiments, the cancer cells are damaged, e.g. prevented from growing or rendered incapable of cell division, etc.

Types of cancer that can be treated using the compounds and methods described herein include but are not limited to: leukemia, lymphoma, sarcoma, neuroblastoma, lung cancer, skin cancer, squamous cell carcinoma of the head and neck, prostate cancer, colon cancer, breast cancer, ovarian cancer, cervical cancer, brain cancer, bladder cancer, pancreatic cancer. The cancer may be at any stage of development, and pre-cancerous cells may also be treated.

The patient or subject that is treated in this manner is usually a mammal, although this is not always the case. Frequently, the mammal is a human, although the methods may also be applied to the treatment of other animals, e.g. in veterinary practice.

The invention also provides methods of inhibiting SphK2 and downstream signaling pathways in a cell. In some embodiments, inhibition of SphK2 is selective, e.g. the compound inhibits SphK2 but not other enzymes, for example, SphK1. In this embodiment, compound K11167 is excluded since it inhibits both SphK2 and SphK1. The methods involve exposing the cells to one or more compounds of the invention, the one or more compounds being present in an amount that is sufficient to inhibit the enzyme, SphK2, usually by at least 50%, in some cases by 60%, 70%, 80%, 90%, 95% or more, or even completely (i.e. 100% inhibition), compared to an untreated control. Those of skill in the art are familiar with methods to measure levels of inhibition of SphK2, e.g. by detecting the amount of a metabolite of SphK2 substrate or compound that participates in the downstream signaling pathway or that is made by or in the pathway, e.g. by measuring an amount or degree of mRNA or protein expression, or the amount of protein modification (e.g. phosphorylation or de-phosphorylation), etc. In some cases, the cells in which these pathways are inhibited are cancer cells.

The invention also provides methods of inhibiting SphK2. In some embodiments, inhibition of SphK2 is selective, e.g. the compound inhibits SphK2 but not other enzymes, for example, SphK1. In this embodiment, compound K11167 is excluded since it inhibits both SphK2 and SphK1 (see FIGS. 5 and 6). The methods of the invention involve bringing the enzyme into contact with one or more compounds of the invention, e.g. by contacting, exposing or otherwise providing access of the compound(s) to the enzyme(s). The kinase may be an isolated purified or partially purified enzyme, or may be within a cell (e.g. in a cell cultured in vitro), or within and organism (in vivo). Generally, the activity of the kinase is inhibited by at least about 20, 25, 30, 35, 40, 45, 50, 55, 60, 65, 70, 75, 80, 85, 90, or 95% or even more, e.g. about 100%, compared to a control enzyme which is not exposed to a compound of the invention. Those of skill in the art are familiar with methodology to measure the activity of enzymes, and of kinases in particular. For example, the ability of a kinase to carry out its usual enzymatic activity may be measured, e.g. by detecting a product of that activity.

The invention also provides methods of inhibiting SphK1 and SphK2 using the compound K11167 (compound 42; see the Scheme in the Examples entitled "Compounds 28-36, 39-40 and 42 of Schemes 2 and 3"). Compound 42 may be used for any of the purposes described herein, e.g. for inhibiting SphK2, for treating diseases associated with SphK2, for killing or damaging cancer cells, for treating cancer, etc. However, its use is not selective for SphK2. Thus, compound 42 may also be used to inhibit SphK1, to treat diseases or conditions associated with SphK1, etc. In further embodiments, compound 42 may be used to inhibit both SphK1 and SphK2, e.g. in vitro or in cells.

The invention also provides methods of inhibiting growth or killing or damaging cells exhibiting positive SphK2 activity. By "positive" SphK2 activity we mean overactivation or overexpression of the kinase. In some embodiments, the cells are cancer cells. The methods involve exposing the cells to one or more compounds of the invention, the one or more compounds being present in an amount that is sufficient to cause the death of the cells, or to cause damage to the cells, e.g. to slow the cells' metabolism, prevent replication, prevent movement, induce apoptosis of the cells, etc. The cells that are killed or damaged may be in vitro or in vivo, i.e. this method may be carried out for clinical purposes (e.g. for the treatment of disease) or in the laboratory (e.g. the compounds of the invention may be used as laboratory reagents.) When a population of cancer cells is exposed to the compounds of the invention, generally about 25, 30, 35, 40, 50, 55, 60, 65, 70, 75, 80, 85, 90, 95, or more, e.g. even 100%, or the cells in the population are damaged or killed, compared to a suitable control population that is not exposed to the compounds.

Other embodiments of the invention include the treatment of diseases or conditions associated with positive SphK2 activity. These methods comprise the step of administering an effective amount of the compound of Formula I and/or Formula II or a composition thereof to a patient in need thereof to inhibit the SphK2 activity. Examples of such disease or conditions include but are not limited to cancer, arthrosclerosis, arthritis, diabetes, obesity, osteoporosis, inflammatory diseases and Alzheimer's disease. An "effective amount" or a "therapeutic amount" refers to an amount that either cures (i.e. symptoms of disease disappear completely or become undetectable), or ameliorates disease symptoms, e.g. by lessening symptoms such as pain, slowing of the growth of a tumor, lengthening the life of a patient, improving the quality of life of a patient, etc.

The invention is further described by the following non-limiting examples which further illustrate the invention, and are not intended, nor should they be interpreted to, limit the scope of the invention in any way.

EXAMPLES

The synthesis of the exemplary compounds is described in Schemes 1-5.

Example 1

Preparation of Compound 26

To a stirred suspension of bromoethylamine hydrobromide 25 (20.5 g, 100 mmol), (Boc)$_2$O (21.8 g, 100 mmol) in dichloromethane (200 mL) was added triethylamine (13.9 mL, 100 mmol) dropwise at 0° C., after added the mixture was stirred at room temperature (rt). overnight, water was added, the separated CH$_2$Cl$_2$ layer was washed with brine, and dried by Na$_2$SO$_4$, remove the solvent to give a colorless oil (20 g).

Example 2

Preparation of Compound 27

A mixture of 2,4-thiazolidinedione (7.9 g, 68 mmol), compound 26 (17.9 g, 80 mmol), K$_2$CO$_3$ (11.1 g, 92 mmol), TBAI (2.5 g, 6.8 mmol) in acetone (100 mL) was stirred at 40° C. for 10 h, suction filter, the filtrate was concentrated under vacuum, the residue was purified by flash column chromatography (Hexane/EA=4/1 to 2/1) to give a white solid (12.3 g).

Example 3

Preparation of Compounds 28-36

A solution of compound 27 (12 mmol), aldehyde (12 mmol) and piperidine (3.6 mmol) in MeOH (60 mL) was stirred at rt. overnight, remove solvent under vacuum, the residue was purified by flash column chromatography (Hexane/EA=8/1) to give a white solid, which was subject to Boc deprotection conditions in ethyl acetate (30 mL) by 4 M HCl in dioxane (15 mL), the solution to give 28-36 as white solid.

Example 4

Preparation of 4-alkoxyphenylpropanal Compounds 14-19

To a stirred solution of compounds 2-7 (891 mg, 5 mmol) and meldrum's acid (720 mg, 5 mmol) in EtOH (5 mL) was added piperidine (two drops), the resulting solution was stirred at rt. overnight, suction filter give a light yellow solid, (731 mg). To the solid and acetic acid (3 mL) in DCM (20 mL) at 0° C. was added sodium borohydride (314 mg, 8.4 mmol) portion wise. The resulting solution was stirred at rt. for 1 h. the solution was dissolved in DCM and washed with brine and water. The organic layer was dried over $Na_2SO_4$ and concentrated under vacuum, the residue was purified by flash column chromatography (Hexane/acetone=5/2) to give a light yellow solid (426 mg). To a solution of above compounds (368 mg, 1.2 mmol) in tetrahydrofuran (7 mL) was added triethylamine (0.334 mL, 2.4 mmol) followed by phenylsilane (0.444 mL, 3.6 mmol). The resulting solution was stirred for 2 hours at room temperature. Water was added to the solution and stirred for 15 minutes. The reaction mixture was dissolved in ether and washed with water, then with brine. The organic layer was dried over $Na_2SO_4$ and concentrated, the residue was purified by flash column chromatography (Hexane/acetone=10/1) to give a light colorless oil.

Example 5

Preparation of 4-alkoxybenzaldehyde Compounds 2-7

A mixture of 4-hydroxybenzaldehyde (10 mmol), bromoalkane (13 mmol), $K_2CO_3$ (13 mmol), DMF (20 mL) was refluxed for 18 h, cooled to rt., water was added, extracted by hexane, concentrated under vacuum, the residue was purified by flash column chromatography to give a light yellow oil.

Example 6

Preparation of Compounds 24, 46, 48 and 50 by Swern Oxidation

DMSO (14 mmol) was added dropvise to a stirred solution of oxalyl chloride (5 mmol) in DCM (20 mL) at −78° C., after added the mixture was stirred at −78° C. for 20 min, then alkanol (4 mmol) was added dropvise and stirred at −78° C. for 1 h, $Et_3N$ (1 mL) was added and the temperature was slowly elevated to rt., then water was added, the separated DCM layer was washed with brine, concentrated under vacuum, the residue was purified by flash column chromatography to give a colorless oil.

Example 7

Preparation of Compound 39 by Reduction

A mixture of compound 31 (KLIII016) (100 mg) and 10% Pd/C (50 mg) in methanol (15 mL) was hydrogenated at rt. overnight, suction filter to remove the catalyst, the filtrate was concentrated under vacuum, then ethyl acetate (1 mL) was added, suction filter, and washed with ethyl acetate to give a white solid.

Example 8

Preparation of Guanidine Analog 42

To a suspension of 31 (KLIII016) (0.2 mmol) in DCM (2 mL) was added triethylamime (0.2 mmol) followed by N,N'-Di-Boc-1H-pyrazole-1-carboxamidine (0.2 mmol), after added the mixture was stirred at rt. overnight, water was added and extracted by DCM, concentrated under vacuum, the residue was purified by flash chromatography (Hexane/Acetone=10/1) give 41 as a colorless oil (88 mg). Compound 41 (80 mg) was dissolved in 2 mL of DCM, 2 mL of HCl (4M in dioxane) was added, the mixture was stirred at rt. for 20 h, filtered to give 28 mg of compound 42 as white solid.

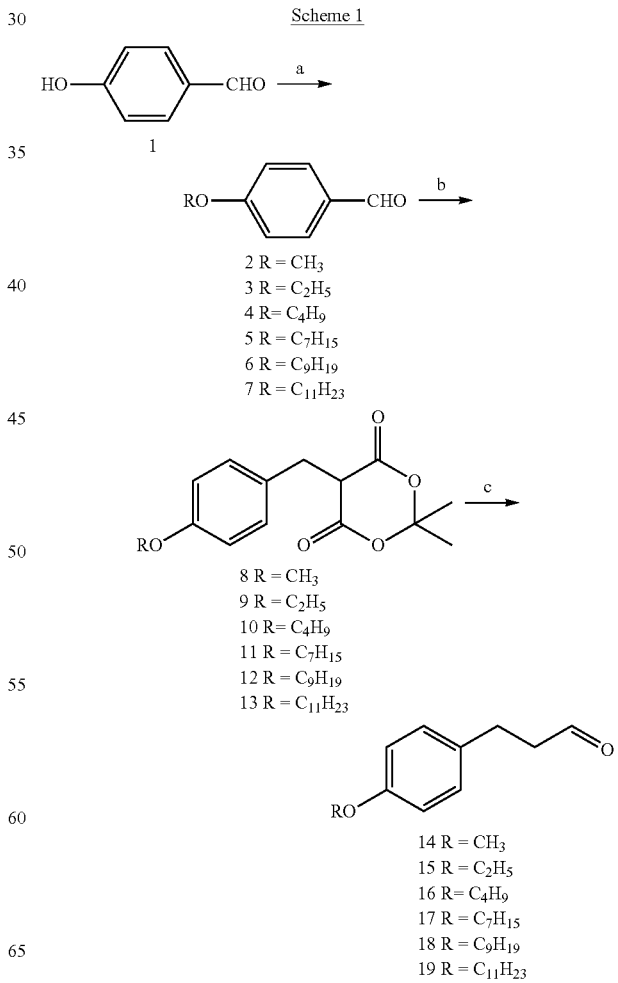

Scheme 1

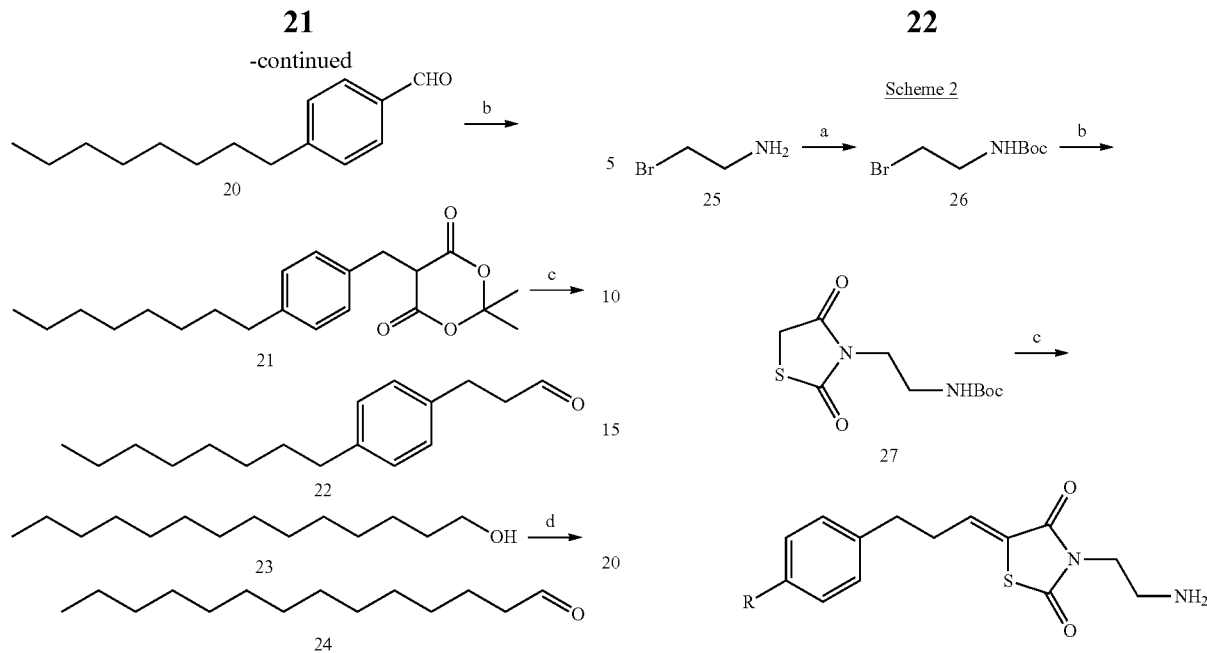

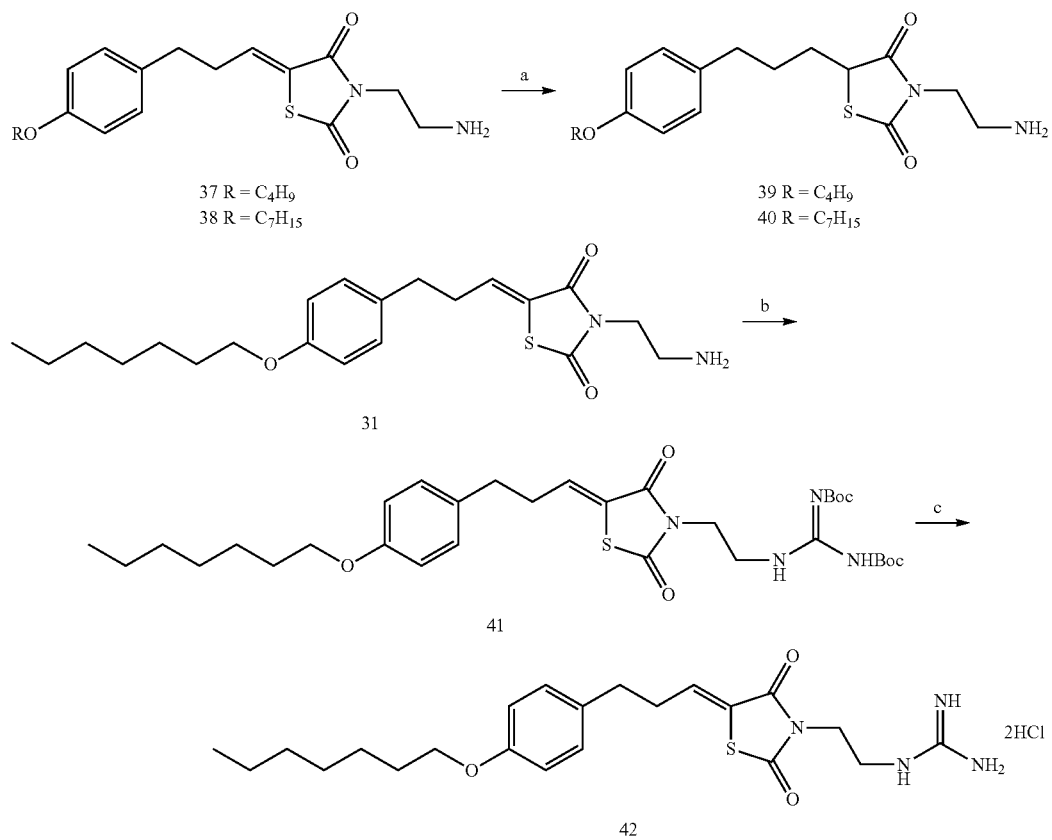

Reagents and conditions: a) Bromoalkane, K$_2$CO$_3$, DMF, reflux; b) i. meldrum's acid, piperdine, EtOH; ii. NaBH$_4$, AcOH, CH$_2$Cl$_2$; c) PhSiH$_3$, Et$_3$N, THF; d) DMSO, (COCl)$_2$, Et$_3$N, CH$_2$Cl$_2$. a) 2,4-thioazolidinedione, K$_2$CO$_3$, TBAI, acetone, 40° C., (b) 4-Butoxypheynlpropanal, Piperidine, ETOH.

Reagents and conditions: a) (Boc)$_2$O, Et$_3$N, CH$_2$Cl$_2$; b) 2,4-thiazolidinedione, K$_2$CO$_3$, TBAI, acetone, 40° C.; c) i. 14-19 or 22 or 24, piperidine, MeOH; ii. 4M HCl in dioxane, ethyl acetate.

Reagents and conditions: a) H2, Pd/C, MeOH; b) Et$_3$N, N,N'-di-Boc—H-pyrazole-carboxamidine, DCM; c) 4M HCl in dioxane, DCM.

Compounds 28-36 39-40 and 42 of Schemes 2 and 3
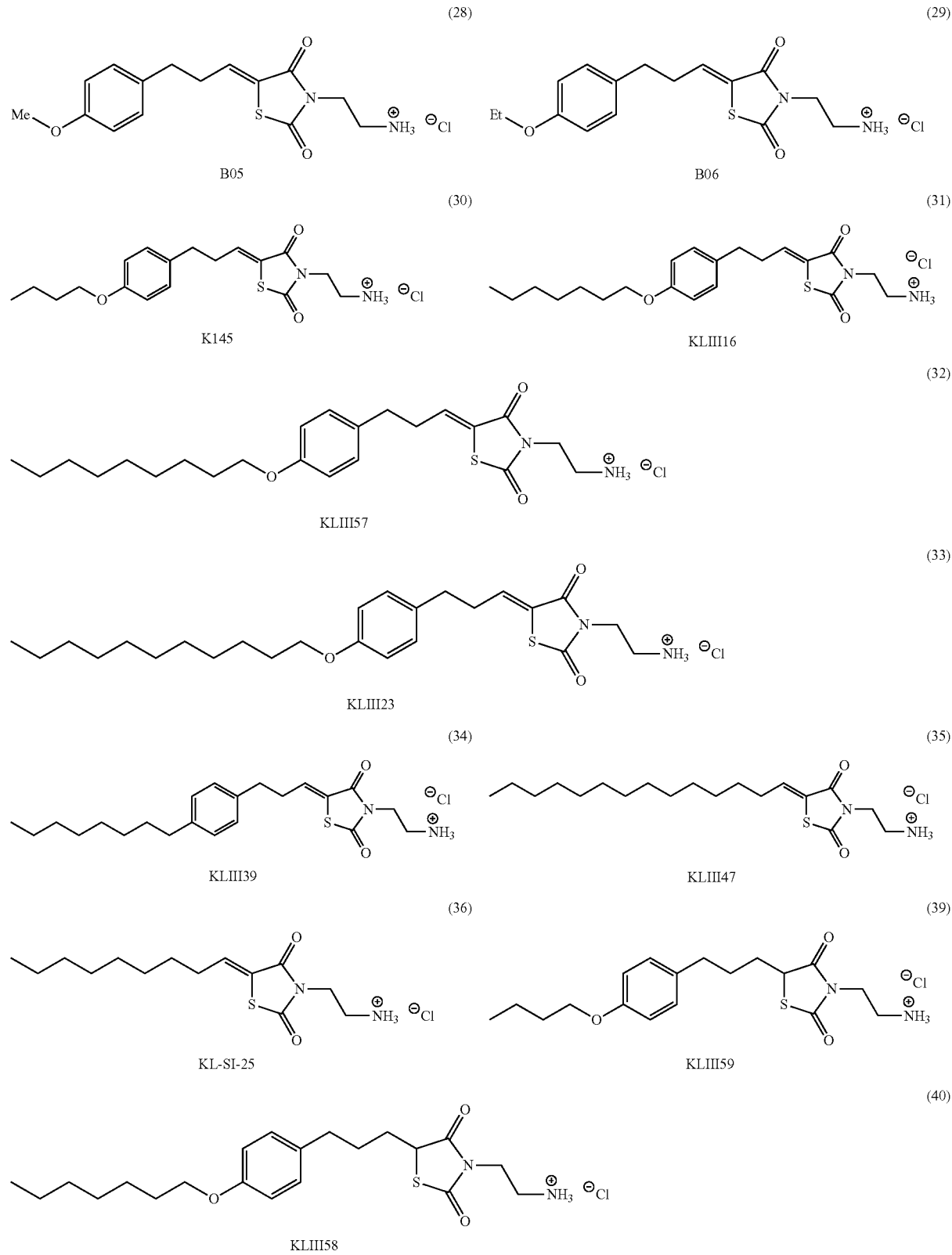

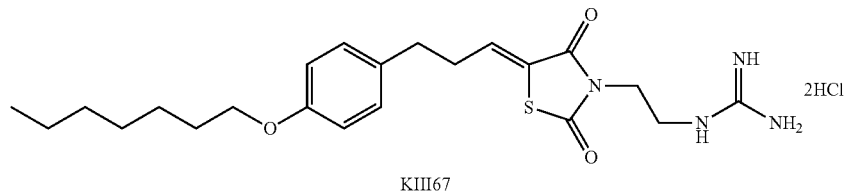
KIII67
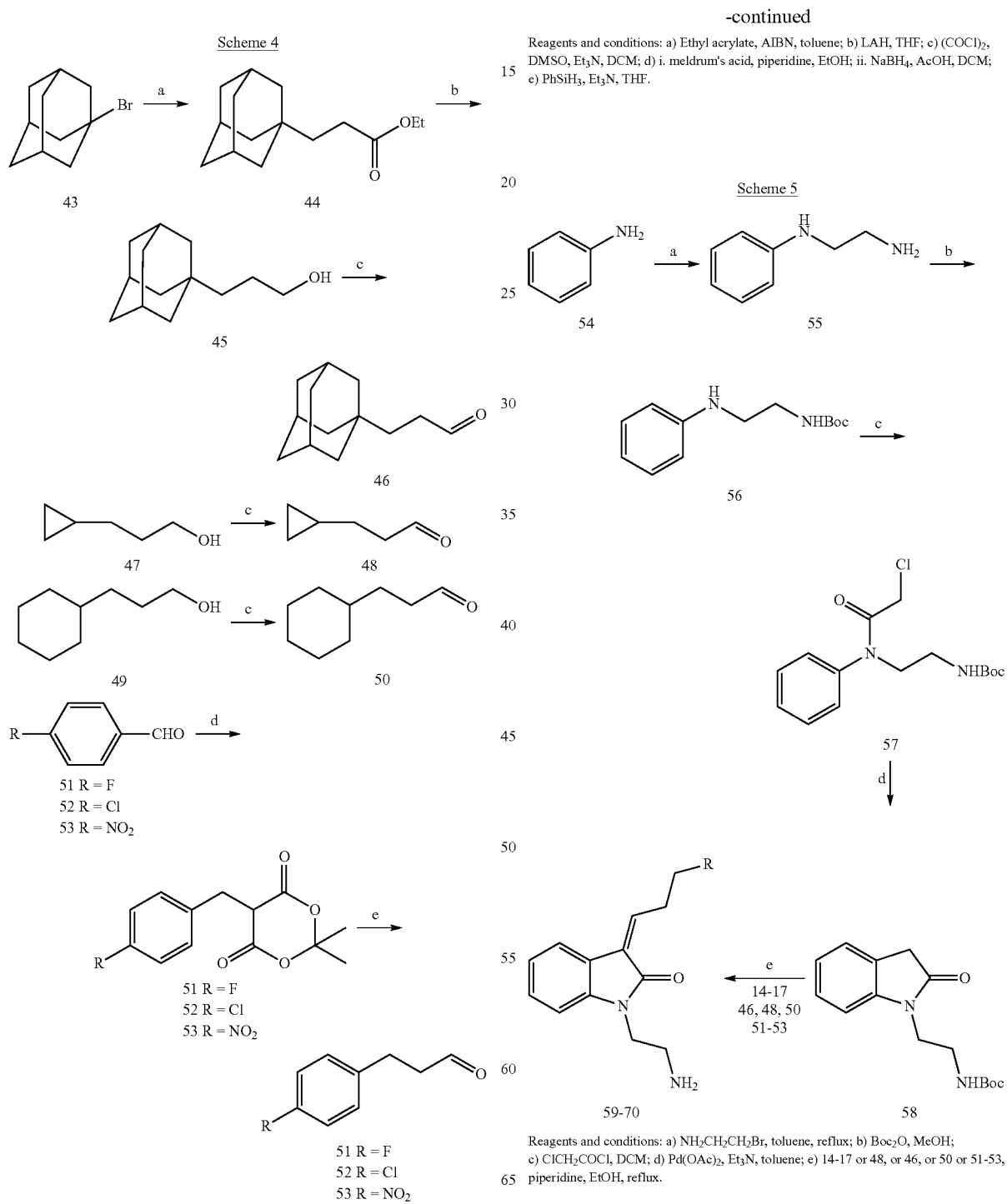
Reagents and conditions: a) Ethyl acrylate, AIBN, toluene; b) LAH, THF; c) (COCl)₂, DMSO, Et₃N, DCM; d) i. meldrum's acid, piperidine, EtOH; ii. NaBH₄, AcOH, DCM; e) PhSiH₃, Et₃N, THF.
Reagents and conditions: a) NH₂CH₂CH₂Br, toluene, reflux; b) Boc₂O, MeOH; c) ClCH₂COCl, DCM; d) Pd(OAc)₂, Et₃N, toluene; e) 14-17 or 48, or 46, or 50 or 51-53, piperidine, EtOH, reflux.

Compounds 59-70 of Scheme 5
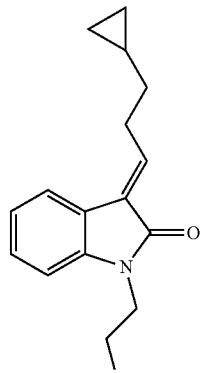
(59) S-II-40
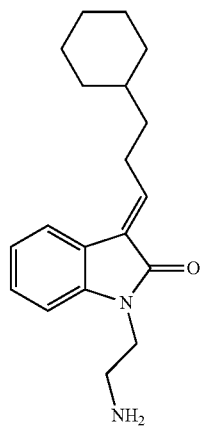
(60) S-II-36
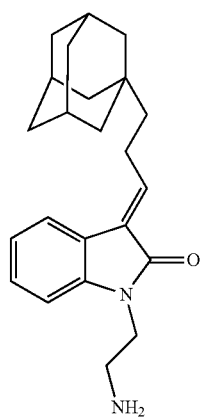
(61) S-II-73
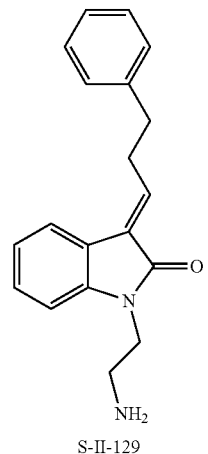
(62) S-II-129
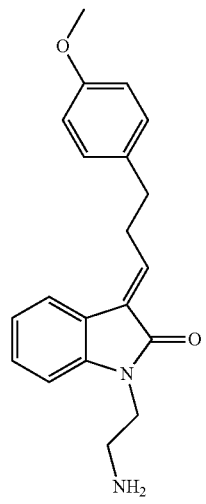
(63) S-II-71
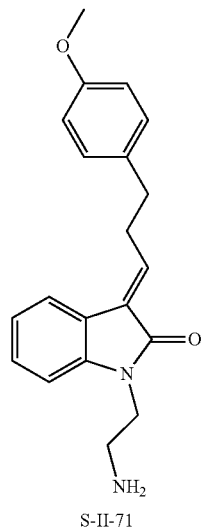
(70) S-II-103

(64)
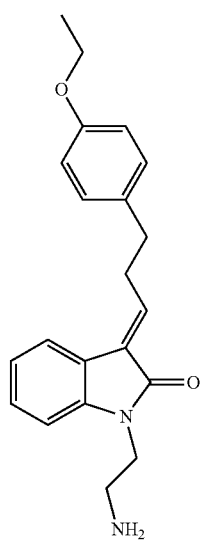
S-II-102
(65)
S-II-78
(66)
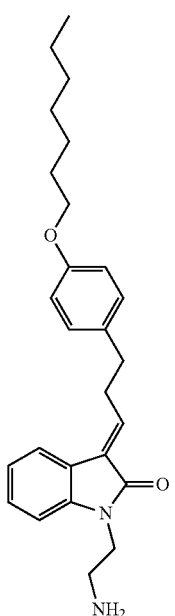
S-II-104
(67)
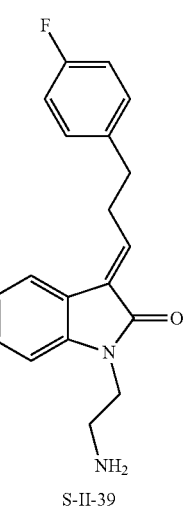
S-II-39
(68)
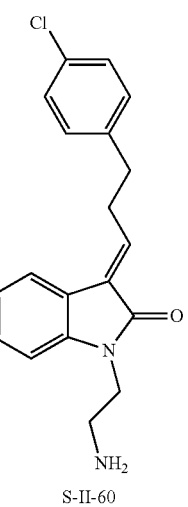
S-II-60

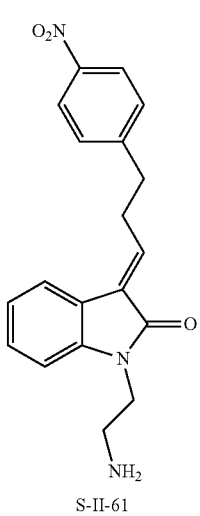

S-II-61

Example 9

KII167 (42)

$^1$H NMR (400 MHz, DMSO-d$_6$): 7.62 (m, 1H), 7.34 (brs, 3H), 7.15-7.13 (d, J=8.5 Hz, 2H), 7.01 (t, J=7.4 Hz, 1H), 6.86-6.83 (d, J=8.5 Hz, 2H), 3.91 (t, J=6.5 Hz, 2H), 3.67 (t, J=4.9 Hz, 2H), 3.39-3.35 (q, J=5.9 Hz, 2H), 2.76 (t, J=7.3 Hz, 2H), 2.53-2.45 (m, 2H), 1.72-1.65 (m, 2H), 1.41-1.39 (m, 2H), 1.37-1.28 (m, 6H), 0.87 (t, J=6.6 Hz, 3H); $^{13}$C NMR (100 MHz, DMSO-d$_6$): 167.3, 164.3, 157.1, 156.9, 137.5, 132.0, 129.3, 125.1, 114.4, 67.3, 40.5, 38.2, 33.0, 32.1, 31.2, 28.7, 28.4, 25.5, 22.0, 13.9.

Example 10

KLIII16 (31)

$^1$H NMR (400 MHz, DMSO-d$_6$): 8.13 (s, 3H), 7.15-7.13 (d, J=8.6 Hz, 2H), 7.01 (t, J=7.4 Hz, 1H), 6.85-6.83 (d, J=8.6 Hz, 2H), 3.91 (t, J=6.5 Hz, 2H), 3.83 (t, J=6.0 Hz, 2H), 3.00 (m, 2H), 2.76 (t, J=7.4 Hz, 2H), 2.53-2.45 (m, 2H), 1.70-1.66 (m, 2H), 1.41-1.37 (m, 2H), 1.35-1.26 (m, 6H), 0.87 (t, J=6.8 Hz, 3H); $^{13}$C NMR (100 MHz, DMSO-d$_6$): 167.6, 164.5, 157.1, 137.4, 132.0, 129.2, 125.2, 114.4, 67.3, 36.5, 33.0, 32.1, 31.2, 28.7, 28.4, 25.5, 22.0, 13.9.

Example 11

KLII157 (32)

$^1$H NMR (400 MHz, DMSO-d$_6$): 8.16 (s, 3H), 7.15-7.13 (d, J=8.6 Hz, 2H), 7.01 (t, J=7.4 Hz, 1H), 6.85-6.83 (d, J=8.6 Hz, 2H), 3.91 (t, J=6.5 Hz, 2H), 3.83 (t, J=6.0 Hz, 2H), 3.00 (m, 2H), 2.76 (t, J=7.4 Hz, 2H), 2.53-2.45 (m, 2H), 1.70-1.64 (m, 2H), 1.40-1.35 (m, 2H), 1.32-1.25 (m, 10H), 0.86 (t, J=6.8 Hz, 3H); $^{13}$C NMR (100 MHz, DMSO-d$_6$): 167.6, 164.5, 157.1, 137.4, 132.0, 129.2, 125.2, 114.4, 67.3, 36.5, 33.0, 32.1, 31.2, 28.9, 28.7, 28.6, 28.5, 25.5, 22.0, 13.9.

Example 12

KLII123 (33)

$^1$H NMR (400 MHz, DMSO-d$_6$): 8.11 (s, 3H), 7.15-7.13 (d, J=8.5 Hz, 2H), 7.01 (t, J=7.4 Hz, 1H), 6.85-6.83 (d, J=8.5 Hz, 2H), 3.91 (t, J=6.5 Hz, 2H), 3.83 (t, J=6.0 Hz, 2H), 3.00 (m, 2H), 2.76 (t, J=7.4 Hz, 2H), 2.53-2.48 (m, 2H), 1.69-1.66 (m, 2H), 1.40-1.37 (m, 2H), 1.27-1.25 (m, 14H), 0.85 (t, J=6.8 Hz, 3H); $^{13}$C NMR (100 MHz, DMSO-d$_6$): 167.6, 164.5, 157.1, 137.4, 132.0, 129.2, 125.2, 114.4, 67.3, 36.6, 33.0, 32.1, 31.2, 28.9, 28.7, 28.68, 28.65, 25.5, 22.0, 13.9.

Example 13

KLI1147 (35)

$^1$H NMR (400 MHz, DMSO-d$_6$): 8.12 (s, 3H), 7.03 (t, J=7.4 Hz, 1H), 3.85 (t, J=6.0 Hz, 2H), 3.02 (m, 2H), 2.24-2.19 (q, J=7.4 Hz, 2H), 1.51-1.48 (m, 2H), 1.31-1.24 (m, 20H), 0.86 (t, J=6.8 Hz, 3H); $^{13}$C NMR (100 MHz, DMSO-d$_6$): 167.6, 164.6, 138.3, 124.9, 36.6, 31.3, 31.1, 29.0, 28.9, 28.8, 28.7, 28.6, 27.2, 22.0, 13.9.

Example 14

KLII139 (34)

$^1$H NMR (400 MHz, DMSO-d$_6$): 8.10 (s, 3H), 7.15-7.13 (d, J=8.2 Hz, 2H), 7.12-7.10 (d, J=8.2 Hz, 2H), 7.02 (t, J=7.4 Hz, 1H), 3.83 (t, J=6.0 Hz, 2H), 3.00 (m, 2H), 2.79 (t, J=7.4 Hz, 2H), 2.55-2.49 (m, 4H), 1.55-1.51 (m, 2H), 1.40-1.37 (m, 2H), 1.26-1.23 (m, 10H), 0.85 (t, J=6.8 Hz, 3H); $^{13}$C NMR (100 MHz, DMSO-d$_6$): 167.6, 164.5, 140.2, 137.4, 137.3, 128.3, 128.1, 125.2, 36.6, 34.7, 32.7, 32.6, 31.2, 30.9, 28.8, 28.6, 22.0, 13.9.

Example 15

K145 (30)

$^1$H NMR (400 MHz, DMSO-d$_6$): 8.08 (brs, 3H), 7.15-7.13 (d, J=8.5 Hz, 2H), 7.01 (t, J=7.4 Hz, 1H), 6.86-6.84 (d, J=8.5 Hz, 2H), 3.92 (t, J=6.4 Hz, 2H), 3.83 (t, J=6.0 Hz, 2H), 3.00 (m, 2H), 2.76 (t, J=7.3 Hz, 2H), 2.53-2.48 (m, 2H), 1.69-1.64 (m, 2H), 1.45-1.39 (m, 2H), 0.92 (t, J=7.3 Hz, 3H); $^{13}$C NMR (100 MHz, DMSO-d$_6$): 167.5, 164.4, 157.1, 137.3, 131.9, 129.2, 125.1, 114.3, 66.9, 36.5, 32.9, 32.1, 30.7, 18.6, 13.6.

Example 16

KL-SI-25 (36)

$^1$H NMR (400 MHz, DMSO-d$_6$): 8.10 (s, 3H), 7.04 (t, J=7.7 Hz, 1H), 3.85 (t, J=6.0 Hz, 2H), 3.04-3.01 (m, 2H), 2.25-2.19 (q, J=7.4 Hz, 2H), 1.52-1.47 (m, 2H), 1.27 (m, 10H), 0.86 (t, J=6.7 Hz, 3H); $^{13}$C NMR (100 MHz, DMSO-d$_6$): 167.6, 164.6, 138.3, 124.9, 36.6, 31.2, 31.1, 28.7, 28.6, 28.5, 27.2, 22.0, 13.9.

Example 17

B26

$^1$H NMR (400 MHz, DMSO-d$_6$): 8.15 (s, 3H), 7.05 (t, J=7.7 Hz, 1H), 3.04-3.00 (m, 2H), 2.20-2.14 (q, J=7.4 Hz, 2H), 1.94 (brs, 3H), 1.69-1.59 (m, 6H), 1.47-1.46 (d, J=2.3 Hz, 6H), 1.27-1.23 (m, 2H); $^{13}$C NMR (100 MHz, DMSO-d$_6$): 167.5, 164.5, 139.1, 124.3, 41.4, 36.5, 36.4, 31.8, 27.9, 25.0.

Example 18

KLII158 (40)

$^1$H NMR (400 MHz, DMSO-d$_6$): 7.74 (s, 3H), 7.09-7.07 (d, J=8.5 Hz, 2H), 6.84-6.81 (d, J=8.5 Hz, 2H), 4.56-4.53 (m, 1H), 3.91 (t, J=6.5 Hz, 2H), 3.72 (t, J=6.2 Hz, 2H), 2.96-2.87 (m, 2H), 2.55 (t, J=7.4 Hz, 2H), 2.10-2.02 (m, 1H), 1.88-1.65 (m, 4H), 1.59-1.52 (m, 1H), 1.43-1.35 (m, 2H), 1.33-1.28 (m, 6H), 0.87 (t, J=6.8 Hz, 3H); $^{13}$C NMR (100 MHz, DMSO-d$_6$): 174.7, 171.5, 156.9, 133.0, 129.2, 114.3, 67.3, 49.6, 36.7, 33.6, 31.2, 31.1, 28.7, 28.5, 28.4, 25.5, 22.0, 13.9.

Example 19

KLII159 (39)

$^1$H NMR (400 MHz, DMSO-d$_6$): 7.91 (s, 3H), 7.10-7.07 (d, J=8.5 Hz, 2H), 6.84-6.82 (d, J=8.5 Hz, 2H), 4.56-4.53 (m, 1H), 3.92 (t, J=6.5 Hz, 2H), 3.73 (t, J=6.2 Hz, 2H), 2.99-2.88 (m, 2H), 2.55 (t, J=7.4 Hz, 2H), 2.11-2.02 (m, 1H), 1.88-1.63 (m, 4H), 1.61-1.52 (m, 1H), 1.47-1.38 (m, 2H), 0.92 (t, J=6.8 Hz, 3H); $^{13}$C NMR (100 MHz, DMSO-d$_6$): 174.7, 171.5, 156.9, 133.0, 129.2, 114.3, 67.0, 49.6, 36.6, 33.6, 31.1, 30.8, 28.5, 18.7, 13.7.

Example 20

Compound 41

$^1$H NMR (400 MHz, CDCl3): 11.4 (s, 1H), 8.44 (t, J=5.5 Hz, 1H), 7.08-7.04 (m, 3H), 6.84-6.82 (d, J=8.6 Hz, 2H), 3.94-3.89 (m, 4H), 3.69-3.65 (q, J=5.8 Hz, 2H), 2.78 (t, J=7.4 Hz, 2H), 2.52-2.47 (q, J=7.6 Hz, 2H) 1.79-1.75 (m, 2H), 1.48-1.34 (m, 20H), 1.32-1.30 (m, 6H), 0.88 (t, J=6.8 Hz, 3H).

Example 21

1-(2-aminoethyl)-3-(3-cyclohexylpropylidene)indolin-2-one (S-II-36)

1H NMR (400 MHz, DMSO): δ 8.1279 (s, 3H), 7.65-7.63 (d, J=7.48, 1H), 7.35-7.31 (t, J=7.2 Hz, 1H), 7.22-7.20 (d, J=7.72 Hz, 1H), 7.11-7.07 (t, J=8.16 Hz, 1H), 6.90-6.86 (t, J=7.76 Hz, 1H), 4.01-3.98 (t, J=6.48 Hz, 2H), 3.03-3.00 (m, 2H), 2.71-2.65 (q, J=7.64 Hz, 2H), 1.74-1.51 (m, 5H), 1.49-1.39 (q, J=7.56 Hz, 2H), 1.26-1.11 (m, 4H), 0.97-0.88 (m, 2H)

$^{13}$C NMR (100 MHz, DMSO): 167.1, 142.2, 142.2, 128.9, 128.4, 126.8, 123.4, 122.2, 121.8, 108.7, 36.8, 36.7, 35.5, 32.6, 30.7, 26.1, 25.7

Example 22

1-(2-aminoethyl)-3-(3-cyclopropylpropylidene)indolin-2-one (S-II-40)

$^1$H NMR (400 MHz, MeOD): δ 7.35-7.33 (d, J=6.88 Hz, 1H), 7.35-7.33 (t, J=6.84 Hz, 1H), 7.16-7.07 (m, 3H), 4.11-4.08 (t, J=6.00 Hz, 2H), 3.27-3.24 (t, J=5.72 Hz, 3H) 2.88-2.83 (q, J=7.44 Hz, 2H), 1.60-1.55 (q, J=7.16 Hz, 2H), 0.51-0.46 (m, 2H), 0.16-0.12 (m, 2H)

$^{13}$C NMR (100 MHz, DMSO): 170.5, 144.4, 143.1, 130.2, 128.5, 125.1, 124.0, 123.7, 109.4, 39.3, 38.7, 34.8, 30.6, 11.7, 5.2.

Example 23

3-(3-(3r,5r,7r)-adamantan-1-yl)propylidene)-1-(2-aminoethyl)indolin-2-one (S-II-73)

$^1$H NMR (400 MHz, DMSO): δ 8.11 (s, 1H), 7.62-7.61 (d, J=7.52 Hz, 1H), 7.35-7.31 (t, J=7.72 Hz, 1H), 7.22-7.20 (d, J=7.84 Hz, 1H), 7.12-7.09 (t, J=7.52 Hz, 1H), 6.91-6.87 (t J=7.84 Hz, 1H), 4.00-3.97 (t, J=6.56 Hz, 2H), 3.04-3.00 (q, J=5.44, 2H), 2.65-2.59 (q, J=8.04 Hz, 2H), 1.99 (s, 3H), 1.71-1.60 (q, J=12.04 Hz, 6H), 1.54 (s, 6H), 1.36-1.32 (m, 2H).

$^{13}$C NMR (100 MHz, DMSO): 167.0, 157.1, 142.1, 140.9, 132.4, 129.3, 129.0, 127.2, 123.5, 122.2, 121.6, 114.4, 114.3, 108.7, 67.0, 66.3, 37.0, 36.6, 32.8, 30.8, 30.4, 18.7, 13.7.

Example 24

1-(2-aminoethyl)-3-nonylideneindolin-2-one (S-II-103)

$^1$H NMR (400 MHz, DMSO): δ7.96 (s, 1H), 7.67-7.65 (d, J=7.56, 1H), 7.34-7.17 (t, J=7.68 Hz, 1H), 7.17-7.16 (d, J=7.8, 3H), 7.11-7.07 (t, J=7.56, 1H), 6.91-6.87 (t, J=7.80, 1H), 3.99-3.96 (t, J=6.32, 2H),2.71-2.65 (q, J=7.40, 2H), 1.61-1.57 (m, 2H), 1.39-1.26 (m, 11H), 0.87-0.83 (t, J=6.60, 3H).

$^{13}$C NMR (100 MHz, DMSO): 142.1, 129.0, 127.0, 123.5, 122.2, 121.7, 36.8, 31.2, 28.8, 28.6, 28.0, 22.0, 13.9.

Example 25

1-(2-aminoethyl)-3-(3-(4-methoxyphenyl)propylidene)indolin-2-one (S-II-71)

$^1$H NMR (400 MHz, DMSO): δ 8.14 (s, 1H), 7.65-7.64 (d, J=7.48, 1H), 7.35-7.31 (t, J=7.72 Hz, 1H), 7.24-7.20 (t, J=8.48, 3H), 7.10-7.06 (t, J=7.60 Hz, 1H), 6.89-6.85 (m, 3H), 4.00-3.96 (t, J=6.52, 2H), 3.01-2.95 (m, 4H), 2.88-2.85 (t, J=6.92, 2H), 2.51-2.49 (m, 3H)

$^{13}$C NMR (100 MHz, DMSO): 167.0, 157.7, 142.1, 141.9, 140.9, 140.6, 132.6, 129.3, 129.2, 129.1, 128.7, 127.2, 123.5, 122.2, 121.8, 121.6, 119.4, 113.8, 108.7, 108.4, 55.0, 37.0, 36.8, 36.8, 36.6, 33.4, 32.8, 30.4, 30.4, 29.3

Example 26

1-(2-aminoethyl)-3-(3-(4-ethoxyphenyl)propylidene) indolin-2-one (S-II-102)

$^1$H NMR (400 MHz, DMSO): δ 8.14 (s, 1H), 7.65-7.64 (d, J=7.48, 1H), 7.33-7.31 (t, J=7.72 Hz, 1H), 7.24-7.20 (m, 3H), 7.10-7.06 (t, J=7.60 Hz, 1H), 6.89-6.85 (m, 3H), 4.00-3.96 (t, J=6.52, 2H), 4.00-3.96 (t, J=6.52 Hz, 3H), 3.01-2.95 (m, 4H), 2.88-2.85 (t, J=6.92, 2H), 2.51-2.49 (m, 3H)

$^3$C NMR (100 MHz, DMSO): 167.1, 142.1, 132.4, 129.3, 129.0, 127.2, 123.6, 121.7, 114.2, 108.6, 62.9, 37.1, 36.8, 32.8, 30.4, 14.7

Example 27

1-(2-aminoethyl)-3-(3-(4-butoxyphenyl)propylidene) indolin-2-one (S-II-78)

$^1$H NMR (400 MHz, DMSO): δ 8.16 (s, 1H), 7.66-7.64 (d, J=7.48, 1H), 7.35-7.31 (t, J=7.72 Hz, 1H), 7.22-7.16 (m,

3H), 7.08-7.07 (t, J=6.92 Hz, 1H), 6.89-6.84 (m, 3H), 4.00-3.97 (t, J=6.56 Hz, 2H),3.94-3.91 (t, J=6.44 Hz, 3H), 3.03-2.95 (m, 4H), 2.87-2.84 (t, J=6.96, 2H),1.70-1.63 (m, 2H), 1.45-1.39 (m, 2H), 0.94-0.90 (t, J=7.36 Hz, 3H)

$^{13}$C NMR (100 MHz, DMSO): 167.1, 142.9, 142.1, 128.9, 126.5, 123.3, 122.2, 121.7, 108.7, 66.3, 108.7, 37.0, 36.7, 36.6, 36.5, 32.0, 28.0, 22.4

Example 28

1-(2-aminoethyl)-3-(3-(4-(heptyloxy)phenyl)propylidene)indolin-2-one (S-II-103)

$^1$H NMR (400 MHz, DMSO): δ 8.06 (s, 1H), 7.66-7.64 (d, J=7.48 Hz, 1H), 7.35-7.31 (t, J=7.72 Hz, 1H), 7.22-7.18 (m, 3H), 7.10-7.06 (t, J=7.56 Hz, 1H), 6.89-6.84 (m, 3H), 3.99-3.95 (t, J=6.32, 2H), 3.93-3.90 (t, J=6.52 Hz, 3H), 3.02-2.95 (m, 4H), 2.87-2.84 (t, J=7.04 Hz, 2H),1.72-1.65 (m, 2H), 1.43-1.17 (m, 8H), 0.88-0.85 (t, J=6.64 Hz, 3H)

$^3$C NMR (100 MHz, DMSO): 167.0, 157.1, 142.1, 140.9, 132.4, 129.3, 129.0, 127.2, 123.6, 122.2, 121.7, 114.4, 108.6, 37.0, 36.7, 32.8, 31.2, 30.4, 28.7, 28.7, 28.4, 25.5, 22.0, 13.9.

Example 29

1-(2-aminoethyl)-3-(3-(4-fluorophenyl)propylidene)indolin-2-one (S-II-39)

$^1$H NMR (400 MHz, MeOD): δ 7.66-7.64 (d, J=7.56, 1H), 7.35-7.27 (m, 3H), 7.13-6.97 (m, 5H), 7.10-7.06 (t, J=6.96 Hz, 1H), 6.90-6.86 (t, J=7.24 Hz, 1H), 4.09-4.06 (t, J=5.88 Hz, 2H), 3.26-3.23 (t, J=6.12 Hz, 2H), 3.08-3.03 (m, 2H), 2.99-2.95 (m, 2H).

$^{13}$C NMR (100 MHz, DMSO): 170.0, 164.2, 161.8, 143.1, 138.0, 131.2, 130.4, 129.0, 125.0, 124.1, 123.5, 116.3, 116.1, 109.5, 39.3, 38.7, 34.6, 32.1

Example 30

1-(2-aminoethyl)-3-(3-(4-chlorophenyl)propylidene)indolin-2-one (S-II-60)

$^1$H NMR (400 MHz, DMSO): δ 7.97 (s, 3H), 7.67-7.65 (d, J=7.52 Hz, 1H), 7.36-7.32 (m, 5H), 7.17-7.15 (d, J=7.80 Hz, 2H), 7.10-7.06 (t, J=6.96 Hz, 1H), 6.87-6.84 (t, J=7.04 Hz, 1H), 3.98-3.94 (t, J=6.28 Hz, 2H), 3.04-2.99 (m, 4H), 2.95-2.91 (m, 2H).

$^{13}$C NMR (100 MHz, DMSO): 140.4, 139.8, 130.7, 129.1, 128.3, 127.4, 123.6, 122.2, 121.6, 108.7, 37.1, 36.7, 33.0, 29.9

Example 31

1-(2-aminoethyl)-3-(3-(4-nitrophenyl)propylidene)indolin-2-one (S-II-61)

$^1$H NMR (400 MHz, MeOD): δ 8.75-8.74 (d, J=7.48 Hz, 3H), 7.67-7.65 (d, J=7.52 Hz, 1H), 7.35-7.2890 (m, 5H), 7.23-7.20 (m, 2H), 7.10-7.06 (t, J=6.96 Hz, 1H), 6.90-6.86 (t, J=7.24 Hz, 1H), 4.00-3.96 (t, J=6.48 Hz, 2H), 3.05-2.99 (m, 4H), 2.95-2.91 (m, 2H).

$^{13}$C NMR (100 MHz, DMSO): δ 168.7, 147.4, 145.1, 135.1, 131.2, 129.9, 123.8, 124.2, 123.2, 115.6, 109.5, 37.9, 38.7, 26.6, 32.1

Example 32

In Vitro Test

SphK1 and SphK2 test

Figure 1A:
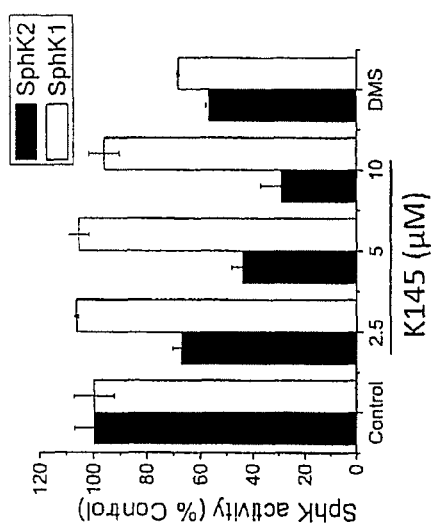
Figure 2:
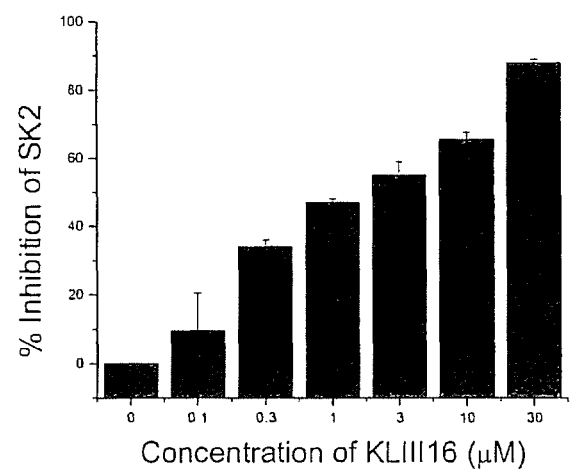
FIG. 2. Compound KLIII16 selectively inhibits SphK2 with a $IC_{50}$ of 1.9 µM

The results from FIGS. 1-6 demonstrate that Formula III (K145) and some other compounds of Formula I and Formula II significantly inhibit SphK2, but not SphK1, thus demonstrating they are selective SphK2 inhibitors. As shown in FIG. 1, Formula III (K145) dose-dependently inhibited SphK2 with a IC$_{50}$ of 5 uM. Significantly, the results of FIG. 2 demonstrates that the potency of this type of SphK2 inhibitors from Formula I can be significantly improved by structural modification as Formula IV (KLIII16) with a longer alkyl chain has an IC$_{50}$ of 1.9 uM compared to that of Formula III (K145).

Kinetic studies of Formula III (K145)

Figure 7:
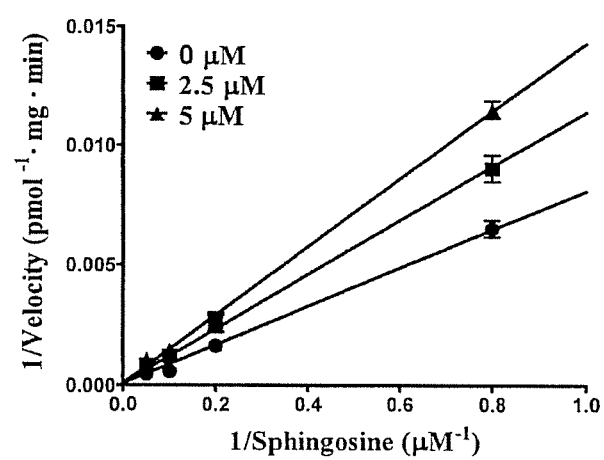
FIG. 7. Kinetic studies of Formula III (K145) in SphK2 and Lineweaver-Burk plot. SphK2 activity was measured with increasing concentrations of sphingosine and the indicated concentrations of K145. Lineweaver-Burk analysis revealed a Vivax of 10820±210 pmol/min per mg of protein, and a $K_i$ of 6.4±0.7 µM for SphK2.

As shown in FIG. 7, the kinetic studies of Formula III revealed that Formula III (K145) is a competitive inhibitor (with the substrate sphingosine) of SphK2 with a Ki value of 4.3±0.7 μM.

Cell Viability Assays in Human Leukemia U937 Cells

Cells were cultured at a density of 5×10$^4$ (U937) or 1×10$^4$ (PC-3, DU145, M12, HT29) cells per well in flat bottomed 96-well plates and treated with various concentrations of test compound at 37° C. (5% CO$_2$). After 24 h, 20 μL of CellTiter 96® Aqueous One Solution Reagent (Promega, Madison, Wis.) was added to each well according to the manufacturer's instructions. After 1 hour, the cell viability was determined by measuring the absorbance at 490 nm using a micro-plate reader.

Figure 8:
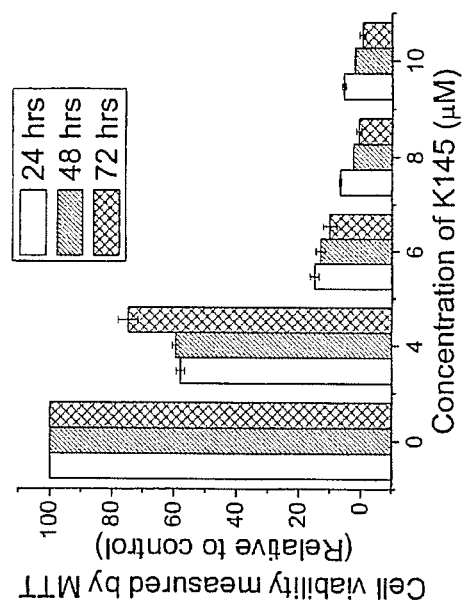
FIG. 8. Compound K145 dose-dependently inhibits the growth of human leukemia U937 cells.

The results are presented in FIG. 8. These results show that Formula III (K145) inhibited the proliferation of tested cancer cells with an IC$_{50}$ at single digit micromolar concentrations.

The results of Table 1 also show that Formula II compounds inhibited the proliferation of human leukemia U937 cells.

TABLE 1

Inhibition of U937 cell proliferation by indicated compounds.*

| Compound | IC$_{50}$ ± SEM | Compound | IC$_{50}$ ± SEM | Compound | IC$_{50}$ ± SEM |
|---|---|---|---|---|---|
| S-II-129 | 2.128 ± 0.006 | S-II-103 | 3.5 ± 0.3 | S-II-104 | 3.9 ± 0.3 |
| S-II-36 | 2.7 ± 0.2 | S-II-71 | 0.92 ± 0.04 | S-II-39 | 2.69 ± 0.06 |
| S-II-40 | 1.16 ± 0.05 | S-II-102 | 0.95 ± 0.11 | S-II-60 | 4.0 ± 0.7 |
| S-II-73 | 4 ± 1 | S-II-78 | 4.6 ± 0.8 | S-II-61 | 3.6 ± 0.2 |

*U937 cells were treated with indicated compounds at various concentrations for 24 hrs, after which cell viability was measured using MTT assay and IC$_{50}$ was calculated.

Western Blot Analysis

Cells (5×10$^5$ per ml) were treated with various concentrations of test compound at 37° C. (5% CO$_2$) for 3 hrs, then stimulated with TPA at a final concentration of 200 nM for 20 min. Samples from whole-cell pellets were prepared and 30 μg protein for each condition was subjected to SDS-PAGE, transferred onto a PVDF membrane, and blocked with 5% fat-free milk for 30 min. The membrane is probed with primary antibodies overnight at 4° C. followed by incubation with horseradish peroxidase-labeled anti-mouse IgG (1:5000, BD Bioscience). The immunoreactive bands are detected by chemilluminescence methods (Pierce) and visualized on Kodak Omat film. The following primary antibodies were used: phospho-p44/42 MAPK (ERK1/2, Thr202/Tyr204), p44/42 MAPK, phospho-p90RSK (Thr359/Ser363), RSK1/RSK2/RSK3 (Cell Signaling).

Blots were reprobed with antibodies against α-tubulin to ensure equal loading and transfer of proteins.

Figure 9:
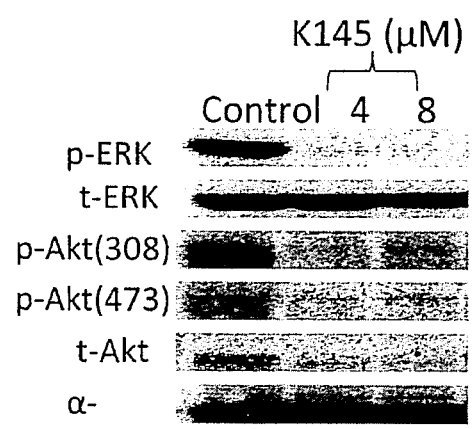
FIG. 9. Compound K145 inhibits the Raf/MEKlERK and PI3K/Akt signaling pathways.
Figure 10:
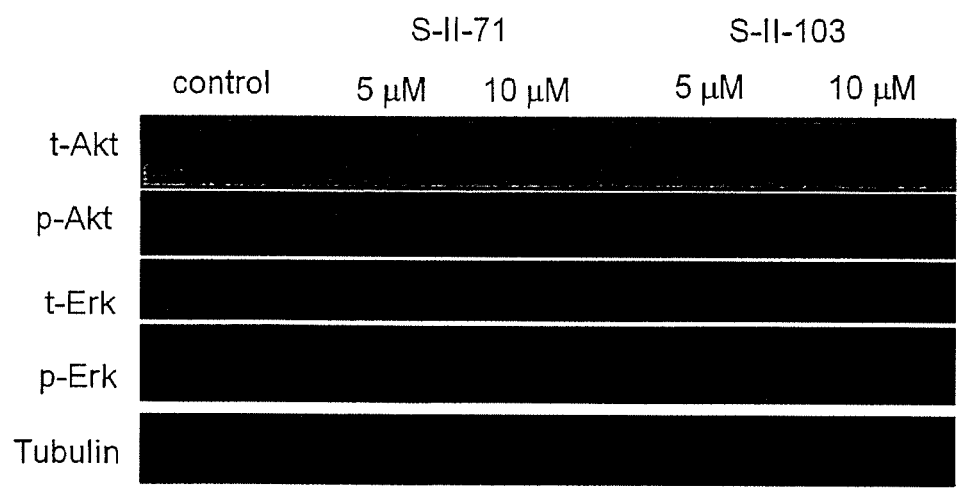
FIG. 10. Compound S-II-71 and S-II-103 inhibit the Raf/MEK/ERK and PI3K/Akt signaling pathways FIG. 11. K145 induces apoptosis in U937 cells in dose- and time-dependent manner.

The results are presented in FIG. 9, which shows that Formula III (K145) significantly inhibited the phosphorylation of both ERK and Akt at 3 μM concentrations. The results are consistent with reported results that SphK execute their effects through, at least through, the Raf/MEK/ERK and PI3K/Akt signaling pathways. As shown in FIG. 10, compounds S-II-71 and S-II-103 also inhibit the Raf/MEK/ERK and PI3K/Akt signaling pathways, which indicates that inhibition of SphK2 by compounds from Formula II, interferes with the Raf/MEK/ERK and PI3K/Akt signaling pathways.

In Vitro Kinase Screening
Cell Apoptosis Assays.

Apoptosis was measured by flow cytometry using annexin V/propidium iodide (PI) as staining reagent. Briefly, after treatment with test compound of varying concentrations for varying intervals (4, 8, 18, 36 hrs), cells were washed twice with cold PBS and then resuspended in 1× binding buffer (10 mM HEPES [N-2-hydroxyethylpiperazine-N'-2-ethanesulfonic acid]/NaOH, pH 7.4, 140 mM NaOH, 2.5 mM $CaCl_2$). The cells were then incubated with annexin V-fluorescein isothiocyanate (FITC) (BD PharMingen, San Diego, Calif.) and 5 μg/mL propidium iodide (PI), and incubated for 15 minutes at room temperature in the dark per the manufacturer's instructions. The samples were analyzed by flow cytometry using a Becton Dickinson FACScan (Becton Dickinson, San Jose, Calif.) within 1 hr to determine the percentage of cells displaying annexin V staining (early apoptosis) or both annexin V and PI staining (late apoptosis).

Figure 11:
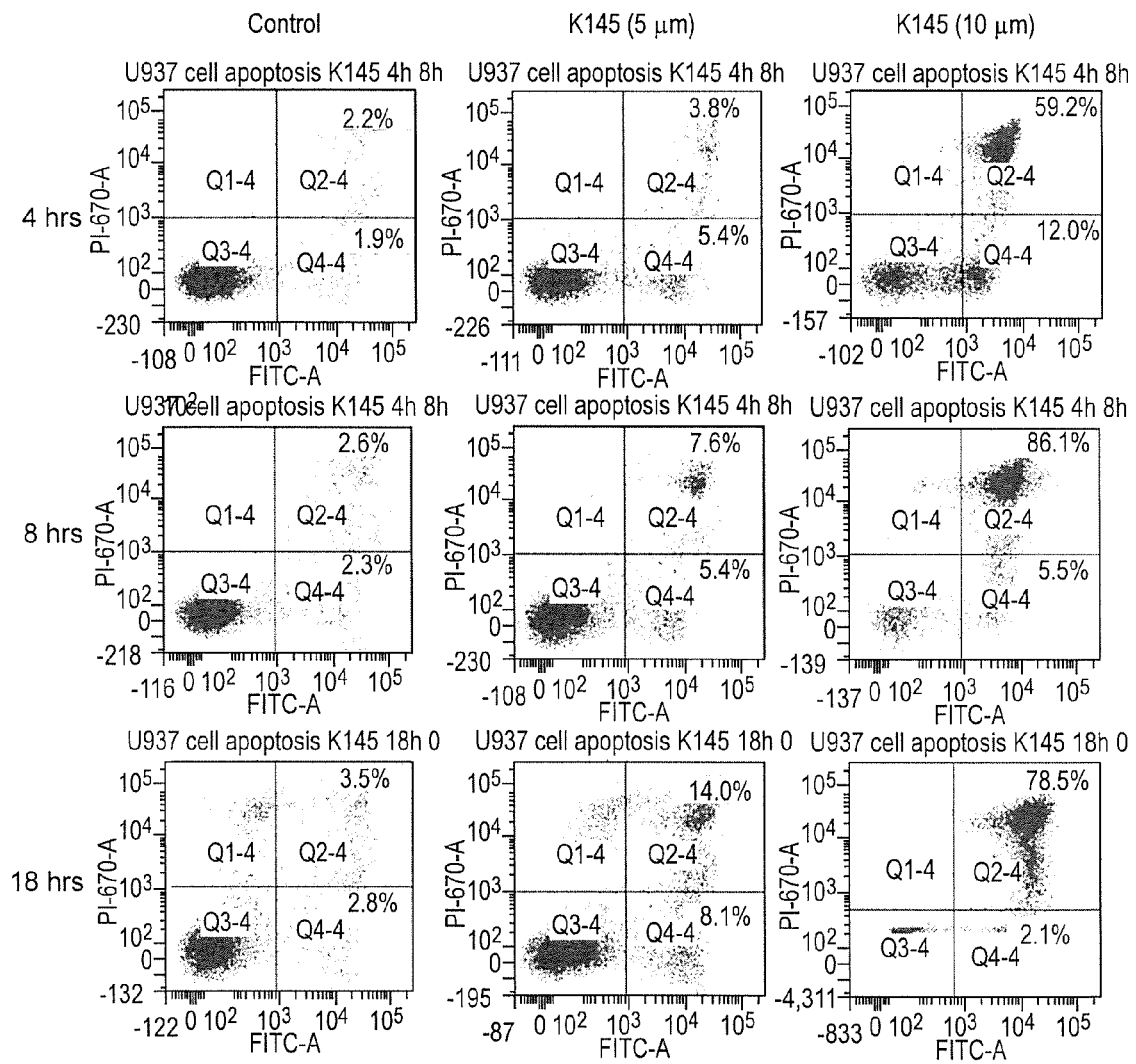
Figure 12:
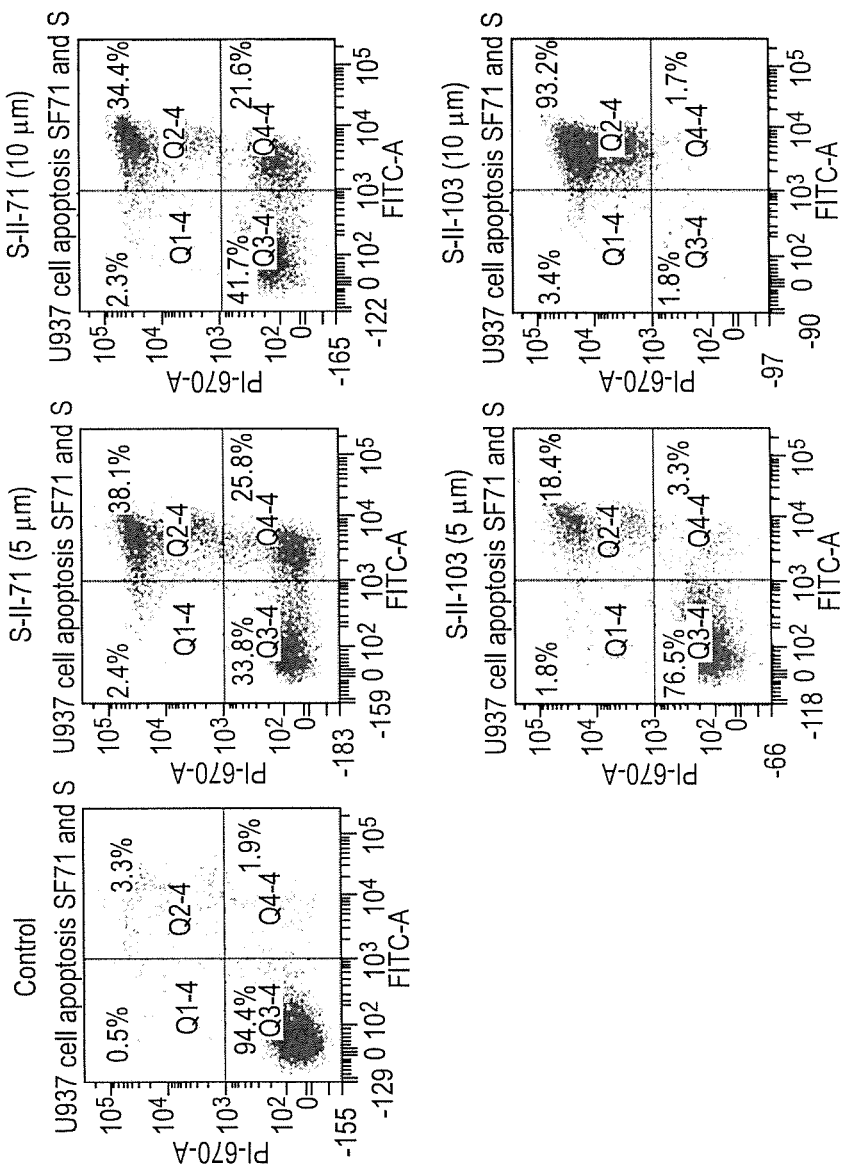
FIG. 12. S-II-71 and S-II-103 induce apoptosis in U937 cells in dose-dependent manner after 24 hrs treatment.

The results are presented in FIG. 11, which shows that Formula III (K145) significantly and dose-dependently induced apoptosis in U937 cells. After 18 hrs, Formula III (K145) significantly induced apoptosis in U937 cells at 5 μM. At 10 μM concentration, Formula III (K145) significantly induced apoptosis at as early as 4 hrs treatment. As shown in FIG. 12, S-II-71 and S-II-103 from Formula II also induced apoptotic effects in U937 cells after 24 hrs treatment. Interestingly, S-II-71 induced both early and late apoptotic effect while S-II-103 mainly induced late apoptotic effects.

Example 18

In Vivo Studies

Anti-proliferation of U937 Xenografts in Nude Mice.

Female nude mice (BALB/c-nu, n=7) were inoculated with $3\times10^7$ U937 cells subcutaneously in the right flank. After 7 days of implant of U937 cells, mice were treated daily with Vehicle (control), or Tamibarotene (15 mg/Kg, positive control), or Formula III (K145) (15 mg/Kg) by i.p. administration. Tumor size was measured every other day. After 18 days treatment, mice were sacrificed and the tumor were removed and weighed.

The results are presented in FIG. 13A, K145 significantly inhibited the growth of U937 tumors in nude mice with a TGI of 44.2%, slightly less potent than tamibarotene (TGI=50.4%) after 17 days treatment. This is also reflected by the tumor weights of treatment groups (FIG. 13B). The tumor growth curve during the treatment course (FIG. 13C) also attests to the anti-tumor effects of K145 in this model. Lastly, as shown in FIG. 13D, the body weights of K145-treated mice remained the same as that of vehicle-treated mice, while tamibarotene treatment caused body weight decreases in the mice. These results strongly suggest that K145 exhibits comparable in vivo anti-tumor activity to tamibarotene, while concomitantly exhibiting less toxicity in this U937 xenograft cancer model.

Anti-Growth of JC Xenografts in Syngenic BALB/c Mice.

Female BALB/c mice (n=12) were injected with $1\times10^6$ JC cells subcutaneously in the flank, and treatment with the compound produced as described in Example 15 i.e. 3-(2-aminoethyl)-5-[3-(4-butoxyphenyl)-propylidene]-thiazolidine-2,4-dione (Formula III-K145, 20 mg/kg and 35 mg/Kg dosage daily (i.p.) was started seven days after the tumor cell injection and stopped at day 15 after tumor injection. Mice were sacrificed at 15 days treatment.

As illustrated in FIG. 14A, treatment of BALB/c mice (n=8) bearing the JC xenograft significantly inhibited tumor growth at both doses with the higher dose being more potent. After 15 days treatment, the mean volume of the JC tumors in the treated-mice at both doses was >50% smaller than that in the vehicle-treated mice. Tumor weights of K145-treated mice were also significantly less than that in vehicle-treated mice in a dose-dependent manner (FIG. 14B). Post-experiment visual evaluation of the tumor samples also confirms the results (FIG. 14D). We analyzed the tumor samples to detect K145, the change of S1P by ESI-MS/MS and the change of signaling pathways by Western blot. As shown in FIG. 14C, K145 was detected in JC tumors and the S1P level was suppressed compared to vehicle, consistent with the results from U937 cells assays. Notably, the p-ERK and p-Akt levels were decreased in the tumor samples compared to the vehicle controls (FIG. 14E), which is consistent with the results from U937 cells (FIG. 9). We did not observe significant changes in body weights and the major organs, such as heart, lung, liver and kidney, thus indicating a lack of general toxicity of K145.

Anti-Proliferation of U937 Xenografts in Nude Mice by K145 through Oral Administration.

We examined the anticancer activity of K145 to inhibit the tumor growth of U937 cells in nude mice (BALB/c-nu) by oral administration to investigate whether it is orally available. In this experiment, K145 was given at 50 mg/kg by oral gavage daily for 15 days and tumor volume and animal weights were measured every other day. Again, tamibarotene (20 mg/kg) was used as positive control. As shown in FIG. 15A, tumor weights of K145-treated mice were significantly less than that in vehicle-treated mice and K145 exhibited better antitumor activity than tamibarotene at tested doses by oral administration (TGI for K145 and tamibarotene are 51.25% and 33.37%, respectively). Visual examination of the tumor samples also confirmed the significant inhibition of U937 tumor growth by K145 (FIG. 15B). Tumor growth curve also demonstrated the superior anti-tumour activity of K145 in these experimental settings (FIG. 15C). As shown in FIG. 15D, at the beginning of the treatment, there was a slight decrease of body weights in K145-treated group but the body weights of this group came back in the remaining course of the study. Collectively, the results of in vivo studies with K145 by oral administration demonstrated that K145 is orally available to inhibit the growth of U937 tumors at 50 mg/kg dose and no apparent toxicity was observed, which is consistent with the results from in vivo studies by i.p. injection administration.

Example 19

In Vitro Target Validation of K145

Next we examined whether K145 affects cellular levels of S1P. Human leukemia U937 cells have been demonstrated to be a good model to test compounds that interfere with the SphK/S1P system and it has previously been shown that S1P is protective against apoptosis of U937 cells. Therefore, we further characterized K145 in U937 cells. As shown in FIG. 16A, K145 is readily taken up by U937 cells in a concentration dependent manner. As shown in FIGS. 16B and 16C, treatment with K145 (10 µM) caused a decrease of total cellular S1P without significant effects on ceramide levels. The inhibitory potency of K145 on cellular level of S1P is somewhat less than its $IC_{50}$ (4.3 µM) determined at recombinant SphK2. This might be due to the fact that many enzymes such as SphK1, SphK2, S1P lyase, and S1P phosphatise, not just SphK2, are involved in the regulation of cellular S1P. The level of ceramide-1-phosphate (C1P) was not significantly affected upon treatment with K145 (10 µM, FIG. 16D), which indicates that K145 does not interfere with CERK and/or ceramide synthase, consistent with the results from recombinant CERK studies. To further confirm its SphK2 selectivity, we then tested the effects of K145 on the phosphorylation of FTY720, a SphK2 specific substrate [35]. As shown in FIG. 16E, K145 inhibited the phosphorylation of FTY720, which further indicates the SphK2 specificity of K145.

We claim:

1. A compound of Formula II:

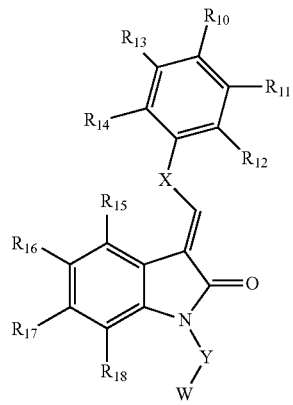

wherein,
R$_{10}$ is selected from the group consisting of: $C_3$-$C_{14}$ alkyl, $C_3$-$C_{14}$ alkoxyl;
R$_{11}$, R$_{12}$, R$_{13}$ and R$_{14}$ may be the same or different and are independently selected from: H, $C_1$-$C_8$ alkyl, $C_1$-$C_8$ alkoxyl, $C_1$-$C_8$ alkylcarbonyl, halogen, hydroxyl, amino, nitro, and cyano;
R$_{15}$, R$_{16}$, R$_{17}$ and R$_{18}$ may be the same or different and are independently selected from the group consisting of: $C_1$-$C_8$ alkyl, $C_1$-$C_8$ alkoxyl, $C_1$-$C_8$ alkylcarbonyl, halogen, hydroxyl, amino, nitro, and cyano;
X is $C_1$-$C_4$ alkyl;
Y is $C_1$-$C_4$ alkyl;
and
W is NR$^{19}$R$^{20}$ where R$^{19}$ and R$^{20}$ may be the same or different and are selected from the group consisting of: H, $C_1$-$C_4$ alkyl; a saturated heterocycle comprising N bonded directly to Y, and an unsubstituted or substituted guanidine moiety.

2. The compound of claim 1, wherein said saturated heterocycle is selected from the group consisting of morpholine, piperidine, piperazine, and pyrrolidine.

3. A method of treating diseases or conditions by inhibiting positive SphK2 activity in a patient in need thereof, comprising the step of administering to said patient a sufficient quantity of at least one compound of Formula II:

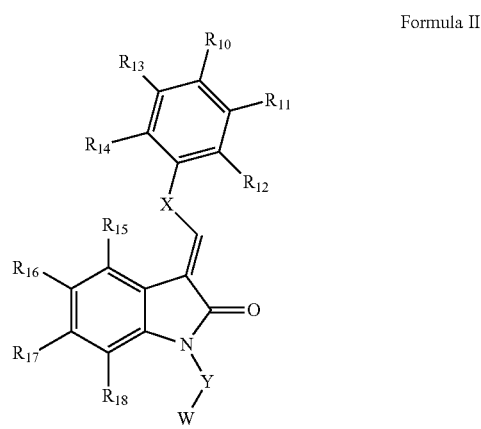

wherein,
in Formula II:
R$_{10}$ is selected from the group consisting of: $C_3$-$C_{14}$ alkyl, $C_3$-$C_{14}$ alkoxyl;
R$_{11}$, R$_{12}$, R$_{13}$ and R$_{14}$ may be the same or different and are independently selected from: H, $C_1$-$C_8$ alkyl, $C_1$-$C_8$ alkoxyl, $C_1$-$C_8$ alkylcarbonyl, halogen, hydroxyl, amino, nitro, and cyano;
R$_{15}$, R$_{16}$, R$_{17}$ and R$_{18}$ may be the same or different and are independently selected from the group consisting of: $C_1$-$C_8$ alkyl, $C_1$-$C_8$ alkoxyl, $C_1$-$C_8$ alkylcarbonyl, halogen, hydroxyl, amino, nitro, and cyano;
X is $C_1$-$C_4$ alkyl;
Y is $C_1$-$C_1$ alkyl;
and
W is NR$^{19}$R$^{20}$ where R$^{19}$ and R$^{20}$ may be the same or different and are selected from the group consisting of: H, $C_1$-$C_1$ alkyl; a saturated heterocycle comprising N bonded directly to Y, and an unsubstituted or substituted guanidine moiety.

4. The method of claim 3, wherein said saturated heterocycle is selected from the group consisting of morpholine, pipieridine, piperazine, and pyrrolidine.

5. The method of claim 3, wherein said disease or condition associated with positive SphK2 activity is selected from the group consisting of: cancer, arthrosclerosis, arthritis, diabetes, obesity, osteoporosis, inflammatory diseases and Alzheimer's disease.

6. A method of inhibiting SphK2, comprising the step of exposing said SphK2 to at least one compound of Formula II:

Formula II

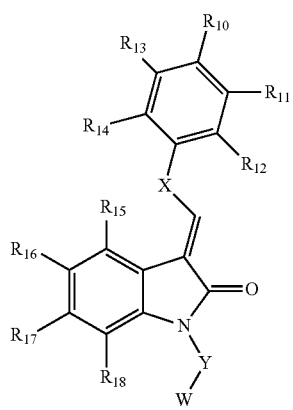

wherein,
in Formula II:
 R$_{10}$ is selected from the group consisting of: C$_3$-C$_{14}$ alkyl, C$_3$-C$_{14}$ alkoxyl;
 R$_{11}$, R$_{12}$, R$_{13}$ and R$_{14}$ may be the same or different and are independently selected from: H, C$_1$-C$_8$ alkyl, C$_1$-C$_8$ alkoxyl, C$_1$-C$_8$ alkylcarbonyl, halogen, hydroxyl, amino, nitro, and cyano;
 R$_{15}$, R$_{16}$, R$_{17}$ and R$_{18}$ may be the same or different and are independently selected from the group consisting of: C$_1$-C$_8$ alkyl, C$_1$-C$_8$ alkoxyl, C$_1$-C$_8$ alkylcarbonyl, halogen, hydroxyl, amino, nitro, and cyano;
 X is C$_1$-C$_4$ alkyl;
 Y is C$_1$-C$_1$ alkyl;
and
 W is NR$^{19}$R$^{20}$ where R$^{19}$ and R$^{20}$ may be the same or different and are selected from the group consisting of: H, C$_1$-C$_4$ alkyl; a saturated heterocycle comprising N bonded directly to Y, and an unsubstituted or substituted guanidine moiety.

7. The method of claim 6, wherein said saturated heterocycle is selected from the group consisting of morpholine, pipieridine, piperazine, and pyrrolidine.

8. The method of claim 6, wherein said SphK2 is present in a cell.

9. The method of claim 8, wherein said cell is selected from the group consisting of a cancer cell, cardiocyte cell, epithelial cell, pancreatic cell, and neuronal cell, and said method includes a step of exposing said cell to said at least one compound of Formula II.

10. A method of inhibiting growth or killing or damaging cancer cells, comprising the step of exposing said cancer cells to a compound of Formula II:

Formula II

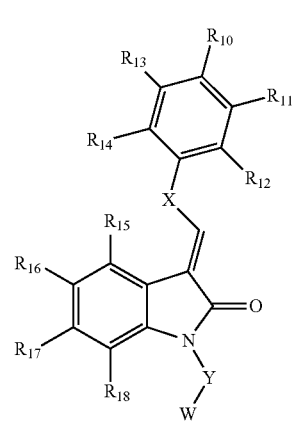

wherein,
 W is NR$_7$R$_8$ where R$_7$ and R$_8$ may be the same or different and are independently selected from H; C$_1$-C$_4$ alkyl; a saturated heterocycle comprising N bonded directly to Y; and an unsubstituted or substituted guanidine moiety;
and wherein
in Formula II:
 R$_{10}$ is selected from the group consisting of: C$_3$-C$_{14}$ alkyl, C$_3$-C$_{14}$ alkoxyl;
 R$_{11}$, R$_{12}$, R$_{13}$ and R$_{14}$ may be the same or different and are independently selected from: H, C$_1$-C$_8$ alkyl, C$_1$-C$_8$ alkoxyl, C$_1$-C$_8$ alkylcarbonyl, halogen, hydroxyl, amino, nitro, and cyano;
 R$_{15}$, R$_{16}$, R$_{17}$ and R$_{18}$ may be the same or different and are independently selected from the group consisting of: C$_1$-C$_8$ alkyl, C$_1$-C$_8$ alkoxyl, C$_1$-C$_8$ alkylcarbonyl, halogen, hydroxyl, amino, nitro, and cyano;
 X is C$_1$-C$_4$ alkyl;
 Y is C$_1$-C$_1$ alkyl;
and
 W is NR$^{19}$R$^{20}$ where R$^{19}$ and R$^{20}$ may be the same or different and are selected from the group consisting of: H, C$_1$-C$_4$ alkyl; a saturated heterocycle comprising N bonded directly to Y, and an unsubstituted or substituted guanidine moiety.

11. The method of claim 10, wherein said saturated heterocycle is selected from the group consisting of morpholine, pipieridine, piperazine, and pyrrolidine.

12. The method of claim 10, wherein said cancer cells are of a type selected from the group consisting of: leukemia, lymphoma, sarcoma, neuroblastoma, lung cancer, skin cancer, head squamous cell carcinoma, neck squamous cell carcinoma, prostate cancer, colon cancer, breast cancer, ovarian cancer, cervical cancer, brain cancer, bladder cancer, and pancreatic cancer.

* * * * *